United States Patent
Arruda et al.

(10) Patent No.: US 9,267,146 B2
(45) Date of Patent: Feb. 23, 2016

(54) INCREASING CELL WALL DEPOSITION AND BIOMASS DENSITY IN PLANTS

(75) Inventors: Paulo Arruda, Campinas (BR); Isabel Rodrigues Gerhardt, Campinas (BR)

(73) Assignee: FIBRIA CELULOSE S.A., Sao Paulo (BR)

( * ) Notice: Subject to any disclaimer, the term of this patent is extended or adjusted under 35 U.S.C. 154(b) by 260 days.

(21) Appl. No.: 13/059,376

(22) PCT Filed: Aug. 21, 2009

(86) PCT No.: PCT/IB2009/006603
§ 371 (c)(1),
(2), (4) Date: Jun. 2, 2011

(87) PCT Pub. No.: WO2010/020868
PCT Pub. Date: Feb. 25, 2010

(65) Prior Publication Data
US 2011/0289629 A1 Nov. 24, 2011

Related U.S. Application Data

(60) Provisional application No. 61/091,075, filed on Aug. 22, 2008.

(51) Int. Cl.
*C12N 15/82* (2006.01)

(52) U.S. Cl.
CPC ........ *C12N 15/8222* (2013.01); *C12N 15/8261* (2013.01)

(58) Field of Classification Search
None
See application file for complete search history.

(56) References Cited

U.S. PATENT DOCUMENTS

2004/0045055 A1 3/2004 Neff

FOREIGN PATENT DOCUMENTS

| WO | WO 2005096805 A2 | * 10/2005 |
| WO | WO 2009/056566 A2 | 5/2009 |
| WO | WO 2009056566 A2 | * 5/2009 |

OTHER PUBLICATIONS

Moreno-Risueno et al. 2007. The family of DOF transcription factors: from green unicellular algae to vascular plants. Mol. Genet. Genomics. 277:379-390.*

International Search Report PCT/IB2009/006603 dated Mar. 24, 2010.

Xiohan Yang et al., "Divergence of the Dof Gene Families in Poplar, Arabidopsis, and Rice Suggests Multiple Modes of Gene Evolution after Duplication", Plant Physiology, Nov. 2006, vol. 142, pp. 820-830.

Yayoi Tsujimoto-Inui et al., "Functional genomics of the Dof transcription factor family genes in suspension-cultured cells of *Arabidopsis thaliana*", Plant Biotechnology 26, 15-28 (2009).

* cited by examiner

*Primary Examiner* — David T Fox
(74) *Attorney, Agent, or Firm* — Arent Fox LLP

(57) ABSTRACT

Modulating in planta expression of a gene encoding WALLDOF, a transcription factor involved in plant cell wall biogenesis, results in increased cell wall deposition and higher plant biomass density.

13 Claims, 14 Drawing Sheets

Fig. 3

CLUSTAL X (1.83) multiple sequence alignment

```
                                                                          1
GSVIVT00006675001_peptide     MDTA-QWPQEI-VVKP--LEEIVTNTC-----PKP----ALERKRARPQKEQALNC
Cotton-WALLDOF1               MDTA-QWPQEI-VVKP--IEEIVTNTC-----PKPT---GLERKIRPQKEQALNC
Eucalyptus-WALLDOF1           MDTA-QWPQEI-VVKP--IEDIVTSTCTAAATPKPSSSSVERKPRPQKEQALNC
GSVIVT00037222001_peptide     MDTA-QWPQGIGVVKP--MES----------SGP----VAERRARPQKDQALNC
WALLDOF                       MDTSTQWPQGIGVVKP--VEG-------------PD---MLERRARPQKEQALNC
Ptr_DOF40                     MDTATQWAQGIGAVNP--MEGS------------RPD---VLERARAQKDQALNC
Gm-DOF21                      MDTA-QWAQGIGVVKQP-MEGSKPPPP-----PPPP---MLERRARPQKDQALNC
Gm-DOF28                      MDTA-QWAQGIGVVKQPTMEGG--SKP-----PPPP---MLERRARPQKDQALNC
                              ***:  **.*  *   .*:   :*                *    *::.*.**:*****
                                     2
GSVIVT00006675001_peptide     PRCNSTNTKFCYYNNYSLSQPRYFCKACRRYWTEGGSLRNIPVGGGSRKNKRS
Cotton-WALLDOF1               PRCNSTNTKFCYYNNYSLTQPRYFCKTCRRYWTEGGSLRNIPVGGGSRKNKRS
Eucalyptus-WALLDOF1           PRCNSTNTKFCYYNNYSLTQPRYFCKTCRRYWTDGGSLRNIPVGGGSRKNKRS
GSVIVT00037222001_peptide     PRCNSTNTKFCYYNNYSLSQPRYFCKTCRRYWTEGGSLRNVPVGGGSRKNKRS
WALLDOF                       PRCTSTNTKFCYYNNYSLSQPRYFCKTCRRYWTEGGSLRNVPVGGGSRKNKRS
Ptr_DOF40                     PRCNSTNTKFCYYNNYSLSQPRYFCKTCRRYWTAGGSLRNVPVGGGSRKNKRS
Gm-DOF21                      PRCNSTNTKFCYYNNYSLSQPRYFCKTCRRYWTEGGSLRNVPVGGGSRKNKRS
Gm-DOF28                      PRCNSTNTKFCYYNNYSLSQPRYFCKTCRRYWTEGGSLRNVPVGGGSRKNKRS
                              ***.************:*********:****** ********:**********

3
GSVIVT00006675001_peptide     SSSSSS--SSSSASSKKLPDLV----PPGCSQSSAQNPKIHLGQDLNLSFF
Cotton-WALLDOF1               STSSSSSISTSLTSSKKLPGLVT---PPSLSQCSTQNPKIHLGQDLNLAFF
Eucalyptus-WALLDOF1           SSSASSSSSSFNSSSKKLPDLIS---TPASN--PNNKVTLHLGQDLNLAFF
GSVIVT00037222001_peptide     TSSSSSS--SSPASSKKLLPDHLITSTPPGFPSSASQNPKIHLGQDLNLAFF
WALLDOF                       SSNPSSSAA-AASEKKFPLDLTQPNFHQSATD---QNPKIHQGPDLNLAYF
Ptr_DOF40                     SSTASTSAAGAAASKKFPLDLTQPNLPHSAS----QNPKIHLGQDLNLAYF
Gm-DOF21                      TPPAPP--SAPAPTKKLS-DLATPNFPQSAS----QDPKIHQGQDLNLAYF
Gm-DOF28                      TPSAPPPSSASAQAKKLP-DLTTPNFPQSAS----QDPKIHQGQDLNLAYF
                              :   ...    :    .*   .             :. .:*:* ****::*

GSVIVT00006675001_peptide     --AAQDFRSVSEFMQMPSIENSNNN----TNNSSKSHITST
Cotton-WALLDOF1               T-ASQGYRSLSELVQLP-LENNNKN----QIPSS----SSS
Eucalyptus-WALLDOF1           NPHHHDFKSISELVQVPSLEASKNH----HISANSSS-AGA
GSVIVT00037222001_peptide     PPPEDYNNSISEFADLSYNGDSKPH----LQNPT----PSS
WALLDOF                       PS--------------------------------------
Ptr_DOF40                     PSADDYSN-LSEFVEIPFDTESNKT---HHQNPNPSSTSPS
Gm-DOF21                      PAEDYSTV--SKFIEVPYSTELDKGTTGLHQNPTSSSTTTS
Gm-DOF28                      PAEDYNTVSMSKLIEVPYNTELDKG--GLHQNPTSSSTPTS 4
GSVIVT00006675001_peptide     SSTSSHISALELIT----GITSRG-LNSFMP-MPIPDPNTVYTTG-FPMQ
Cotton-WALLDOF1               SPTTSQISALELIT----GITSRG-FNSFIP-MPVPDPNTVYTPGN-FPMQ
Eucalyptus-WALLDOF1           SMAPPQISALELIS----GITSRGSFSSFMS-MPVHDPGSVYTPGLFALP
GSVIVT00037222001_peptide     SSSHHHISAMELIKS--TGIASRG-LGSFMP-MSVSDSNSIYSSG-FPLQ
WALLDOF                       -----HISAMELIKS--SGMNPRG-FSAFMSIPAASDSNN-MFSTGFPLQ
Ptr_DOF40                     HHHHHHVSPMEFIKS--TAMNSRG-FSAFMSIPPLSDSNNTMFSTGFPLQ
Gm-DOF21                      ASS--QISAMELIKTGIAAASSRG-LNSFM---PMYNST-----HGFPLQ
Gm-DOF28                      ASSHHQISAMELIKTGIAAASSRG-LNSFM---PMYNSTH----HGFPLQ
                              : :.: *:*.    .     **  :.:*:    . :.       *.:

5                       6
GSVIVT00006675001_peptide     EFKP---TLNFSLDGLGSG-YGSI-QGVQ--G-SSSGRLLFP-FEDLKQV
Cotton-WALLDOF1               DFKP---TLNFSLDGLGNG-YGSL-HGVQ--E-TT-GRLLFP-FEDLKQV
Eucalyptus-WALLDOF1           DFKP---TLNFSLDGLGSGGYRSL-PSVQEGG-TNGGRLLFP-FEDLKPV
GSVIVT00037222001_peptide     EFKP---TLNFSLDGFQSG-YGSL-QGVQ----ESGARLLFP-LEDLKQV
WALLDOF                       EFKP--STQNFSLEGFESG-YSNI-QGVHETG--SSARLLFP-VEDLKQQ
Ptr_DOF40                     EFK---STQNFSLEGLESG-YSNT-QGVHETC--GSARLLFP-IEDLKQQ
Gm-DOF21                      DFKPPH-QLNFSLEGFENG-YGGL-QGIQEGP-TGGARILFPTVEDLKQQ
Gm-DOF28                      DFKPPHHQLNFSLEGFDNGTYGGLHQGIQEDPTTGGARILFPTVEDLKQQ
                              :**     ****:*.* . . .:.            *:*** .***

7
GSVIVT00006675001_peptide     SSTADHIEQTREQGD----STGYWTGMLGGGSW
Cotton-WALLDOF1               STTTD-IDQHKDQGD----STGYWTGMLGGGSW
Eucalyptus-WALLDOF1           SSTSDMEQNRGDQGD----SLGYWSGMLGGGSW
GSVIVT00037222001_peptide     SNTTEFEQSRGVQGD----SAGYWNGMLGGGSW
WALLDOF                       VPSNAEFERINARGQGDGAP-GYWNGMLGGGSW
Ptr_DOF40                     VPSNTEFEQN-TREQRDNAPVGYWNGMLGGGSW
Gm-DOF21                      VPSTNEFD-QQNRSQ-EGSAIGYWNGMLGGGSW
Gm-DOF28                      VPSTNEFDHQQNRSQ-EGSAIGYWNGMLGGGSW
                               :     :      :    . ***.********
```

Fig. 4

CLUSTAL X (1.83) multiple sequence alignment

```
Sb04g032040.1                       ----------------MEEMLMAGNANPNQNPN-PPPPAPSAPGAQ-RA
Zea1                                MDAAQWHQHQGLGLGKPMEEMLMAGNANLNQNPN-PPPPAPSAPGAQ-RA
LOC_Os02g45200.1|12002.m33816|      MDAAHWH--QGLGLVKPMEEMLMGANPNPNGSSNQPPPPPSSAASAQ-RP
Sb06g025680.1                       ----------------MEEMLMAANAGAANPSQGSNNPNPPAPAP----
Zea2                                MDAAHWQ--QGLGLVKPMEEMLMAANAGAANPSQ-SSNPNPPAPAPS-LA
LOC_Os04g47990.1|12004.m09738|      MDAAHWH--QGLGLVKPMEEMLMAANAAAG------ANPNPAATAPSSVT
                                                    ******.*.         . ..*...

1
Sb04g032040.1                       GAPAAGAAAAPSAGATGGPAGAGTERRARPQKEKALN
Zea1                                GAPAAVAAAPPSAGATG---GAGTERRARPQKEKALN
LOC_Os02g45200.1|12002.m33816|      IAPPAAGAAAG-AGAAG--AGAGTERRARPQKEKALN
Sb06g025680.1                       GGALRGG-GAPAAPLAG---AGSTERRARPQKEKALN
Zea2                                PGGLLGG-GAP-APLAG---AGSTERRARPQKEKALN
LOC_Os04g47990.1|12004.m09738|      GGALRGGGGGGAPPVAGGAGAGSTERRARPQKEKALN
                                      .    .   .:*     ....*************

2
Sb04g032040.1                       CPRCNSTNTKFCYYNNYSLQQPRYFCKTCRRYWTEGGSLRNVPVGGGSRKNKRSSSAVSS---
Zea1                                CPRCNSTNTKFCYYNNYSLQQPRYFCKTCRRYWTEGGSLRNVPVGGGSRKNKRSSSAVSSAAA
LOC_Os02g45200.1|12002.m33816|      CPRCNSTNTKFCYYNNYSLQQPRYFCKTCRRYWTEGGSLRNVPVGGGSRKNKRSSSSVVP-SA
Sb06g025680.1                       CPRCNSTNTKFCYYNNYSLQQPRYFCKTCRRYWTEGGSLRNVPVGGGSRKNKRSSSSAS----
Zea2                                CPRCNSTNTKFCYYNNYSLQQPRYFCKTCRRYWTEGGSLRNVPVGGGSRKNKRSSSSAS----
LOC_Os04g47990.1|12004.m09738|      CPRCNSTNTKFCYYNNYSLQQPRYFCKTCRRYWTEGGSLRNVPVGGGSRKNKRSSSSAASASP
                                    ************************************************************:..

3
Sb04g032040.1                       AAAASTSAAMSG------TVSVG-LPAKNPKLMHEGAHDLNLAFPHING
Zea1                                AAAASTSAAMSG------TVPVG-LAAKNPKLMHEGAHDLNLAFPHING
LOC_Os02g45200.1|12002.m33816|      AASASTSAAVSG------SVPVG-LAAKNPKLMHEGAQDLNLAFPEHHG
Sb06g025680.1                       ASASTSASVTSS-----SMASAEGAAASKNPKLAHEGAHDLNLAFPHIGG
Zea2                                ASASTSGSVTSS-----SMASTAG-AGSKNPKLAHEGAHDLNLAFPHIGG
LOC_Os04g47990.1|12004.m09738|      ASASTANSVVTSASMSMSMASTGG-GASKNPKLVHEGAQDLNLAFPHIGG
                                    *::::: :. :.       : . *  :***** ****:******** *

4
Sb04g032040.1                       RALQPP-EFPAFPSLESSSVCNPGAAGMVGNGAAGRG---NGALSAMELI
Zea1                                RALQPP-EFPAFPSLESSSVCNPGAA-MLGNGAAGRG---NGALSGLELI
LOC_Os02g45200.1|12002.m33816|      RALQPP-EFTAFPSLESSSVCNPGGNLAAANGAGGRGS--VGAPSAMELI
Sb06g025680.1                       --LHAP-EFAAFPSLESSNVCNPGGG-MTSNGRGGGAPAVGALSAMELI
Zea2                                --LHAP-EFAAFPSLESSNVCNPGGG-MTSNGRGGGAPAVGALSAMELI
LOC_Os04g47990.1|12004.m09738|      --LQAPGEFPAFPSLESSSVCNPGGP-MGTNGRGG-----GALSAMELI
                                       *:.* **.*******.*****.     ** .*      **:.*.***

5
Sb04g032040.1                       RSTGCYVPL-QHVQLGMPAEYAAAGFALGEFRMPPPPQ-----SHSVLGFSLDTHQ
Zea1                                RSTGCYVPL-QHFQLGMPAEYAAAGFSLGEFRVPPPPQ-----SQSVFGFSLDTHQ
LOC_Os02g45200.1|12002.m33816|      RSTGCYVPLPQMAPLGMPAEYAAAGFHLGEFRMPPPPQQQQQQAQTVLGFSLDTHQ
Sb06g025680.1                       RSSGCYMPLQMPM--QMQGDYTAAEFALGDFRTPPPPP-----SQSVLGFSLDAHQ
Zea2                                RSSGCYMPLQMPMPMAMPGDYTAAGFALGEYRTPPPPP-----SQSVLGFSLDAHQ
LOC_Os04g47990.1|12004.m09738|      RSTGCYMPLQVPM--QMPAEYATPGFALGEFRAPPPPQS----SQSLLGFSLDAHQ
                                    **.***.**    *   .:*::. * **.:* ****      :::.*****.*

6
Sb04g032040.1                       TGGVGGAGGY---SAGLQ--DSAAGRLLFPFEDLKPAVSAAAG
Zea1                                TGGVGGAGGY---SAGLQ--ESAAGRMLFPFEDLKPAVSAAGG
LOC_Os02g45200.1|12002.m33816|      AGAGGGSGVFGACSAGLQ--ESAAGRLLFPFEDLKPVVSAAAG
Sb06g025680.1                       PGSGAAAAGYG-SSAGLQGVTENAGRLLFPFEDLKPEVSSGGG
Zea2                                PGSGATAAGYG-SSAGLQGVPENAGRLLFPFEDLKPVVGSEGG
LOC_Os04g47990.1|12004.m09738|      SVGGPSAAGFG-SSAGLQGVPESTGRLLFPFEDLKPTVSSGTG
                                    .  .  :. :    *****    .**:********* *.: *

7
Sb04g032040.1                       GG--GASNGADH-----HQYEHSKDQAAGDGGSGPSGVTGGHETP-GFYS
Zea1                                G----ASNGADH-----HHYEHSKDQAAGDGG-GASGVTGGHEAPAGFYS
LOC_Os02g45200.1|12002.m33816|      D----ANSGGD------HQYDHGKNQ--GGGG----GVIGGHEAP-GFYN
Sb06g025680.1                       GVAGGATGGAGDGNSNHNQFDHNKEQDGGGGP----G--AGHDTP-GFYS
Zea2                                ---GGATGGASDGNSSHTQFDHNNKEQGGGGT----G--AGHDTP-GFYS
LOC_Os04g47990.1|12004.m09738|      ---GGGASGGGAGVDGGHQFDHGKEQQAGGGG----GGPGGHDTP-GFYN
                                        .*..     :::*.:.: *.*    *    . **::* ***.

Sb04g032040.1                       NSLIGNGSSNGGGG--PW
Zea1                                NSMIGNGSSNGGGG--SW
LOC_Os02g45200.1|12002.m33816|      SSMIGNGSSNGGGGGGSW
Sb06g025680.1                       G-MIGG-SGASW------
Zea2                                G-MIGG-SGASW------
LOC_Os04g47990.1|12004.m09738|      G-MIGGGSGTSW------
                                    . :**. *.. .
```

(A) Order and composition of WALLDOF motifs

(B) Amino acid consensus sequence of WALLDOF motifs

| Motif | Motif consensus | Remark |
|---|---|---|
| 1 | R[PA]QK[DE][KQ]ALN | |
| 2 | CPRCNSTNTKFCYYNNYSLTQPRYFCKTCRRYWTDGGSLRNIPVGGGSRKNK | DOF signature |
| 3 | H[EQ]G[APQ][-HQ]DLNL[AS][FY]P | |
| 4 | S[APG][LM]ELL | |
| 5 | [LFQ][GN]FSL[DE] | |
| 6 | R[ILM]LFP[-T][FIVL]EDLK[PQ] | |
| 7 | G[FY]W | |

SEQUENCE LISTING

<160> NUMBER OF SEQ ID NOS: 30

<210> SEQ ID NO 1
<211> LENGTH: 768
<212> TYPE: DNA
<213> ORGANISM: Populus sp.

<400> SEQUENCE: 1

| | |
|---|---|
| atggatactt ctactcagtg gccacagggg attggtgttg ttaaaccagt ggaagggcct | 60 |
| gatatgttag agagaagggc aaggccgcaa aaggaacaag ctttgaattg tccaaggtgc | 120 |
| acttcgacca atacaaaatt ttgttactac aacaactata gtctgtctca gccaagatac | 180 |
| ttttgcaaga cttgtagaag gtactggact gaaggtgggt ctttaagaaa tgttcctgtt | 240 |
| ggtggtggtt cgagaaagaa caagagatca tcaagtaatc catcatcatc agctgcggca | 300 |
| gcatctgaaa agaagtttcc tcttgatctg acccagccaa atttccatca gtcagctact | 360 |
| gatcaaaacc ctaagatcca tcaaggccca gatctaaacc tagcttaccc tccatctcat | 420 |
| atctcagcta tggagcttct caagagttct ggaatgaatc caaggggatt tagtgctttc | 480 |
| atgtcaattc ccgcagcgtc tgattcaaac aacatgtttt caactgggtt tcctttgcaa | 540 |
| gaattcaagc catcaaccca gaacttttct ttagaagggt ttgaaagtgg gtatagtaac | 600 |
| attcaaggtg tgcatgagac tggtagtagt gcaaggcttt tgtttcctgt cgaggacttg | 660 |
| aagcagcagg ttccaagtaa tgctgaattt gagcggatta atgctagagg caaggagat | 720 |
| ggtgctcctg gctattggaa tggaatgtta ggtggtggat catggtaa | 768 |

<210> SEQ ID NO 2
<211> LENGTH: 255
<212> TYPE: PRT
<213> ORGANISM: Populus sp.

<400> SEQUENCE: 2

Met Asp Thr Ser Thr Gln Trp Pro Gln Gly Ile Gly Val Val Lys Pro
1               5                   10                  15

Val Glu Gly Pro Asp Met Leu Glu Arg Arg Ala Arg Pro Gln Lys Glu
            20                  25                  30

Gln Ala Leu Asn Cys Pro Arg Cys Thr Ser Thr Asn Thr Lys Phe Cys
        35                  40                  45

Tyr Tyr Asn Asn Tyr Ser Leu Ser Gln Pro Arg Tyr Phe Cys Lys Thr
    50                  55                  60

Cys Arg Arg Tyr Trp Thr Glu Gly Gly Ser Leu Arg Asn Val Pro Val
65                  70                  75                  80

Gly Gly Gly Ser Arg Lys Asn Lys Arg Ser Ser Ser Asn Pro Ser Ser
                85                  90                  95

Ser Ala Ala Ala Ala Ser Glu Lys Lys Phe Pro Leu Asp Leu Thr Gln
            100                 105                 110

Pro Asn Phe His Gln Ser Ala Thr Asp Gln Asn Pro Lys Ile His Gln
        115                 120                 125

Gly Pro Asp Leu Asn Leu Ala Tyr Pro Pro Ser His Ile Ser Ala Met
    130                 135                 140

Glu Leu Leu Lys Ser Ser Gly Met Asn Pro Arg Gly Phe Ser Ala Phe
145                 150                 155                 160

Met Ser Ile Pro Ala Ala Ser Asp Ser Asn Asn Met Phe Ser Thr Gly
                165                 170                 175

Phe Pro Leu Gln Glu Phe Lys Pro Ser Thr Gln Asn Phe Ser Leu Glu
            180                 185                 190

```
Gly Phe Glu Ser Gly Tyr Ser Asn Ile Gln Gly Val His Glu Thr Gly
        195                 200                 205

Ser Ser Ala Arg Leu Leu Phe Pro Val Glu Asp Leu Lys Gln Gln Val
    210                 215                 220

Pro Ser Asn Ala Glu Phe Glu Arg Ile Asn Ala Arg Gly Gln Gly Asp
225                 230                 235                 240

Gly Ala Pro Gly Tyr Trp Asn Gly Met Leu Gly Gly Gly Ser Trp
                245                 250                 255

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atccatggat acttctactc agtggccaca gg                                 32

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
actctagatt accatgatcc accacctaac attc                               34

<210> SEQ ID NO 5
<211> LENGTH: 4
<212> TYPE: DNA
<213> ORGANISM: Unknown
<220> FEATURE:
<223> OTHER INFORMATION: Description of Unknown: cis-regulatory element
      common core oligonucleotide

<400> SEQUENCE: 5 aaag                                                                 4

<210> SEQ ID NO 6
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Ile Leu Lys Cys Pro Arg Cys Asp Ser Met Asn Thr Lys Phe Cys
1               5                   10                  15

Tyr Tyr Asn Asn Tyr Asn Leu Ser Gln Pro Arg His Phe Cys Lys Thr
            20                  25                  30

Cys Arg Arg Tyr Trp Thr Lys Gly Gly Ala Leu Arg Asn Val Pro Val
        35                  40                  45

Gly Gly Gly Cys Arg Lys Asn Lys Arg
    50                  55

<210> SEQ ID NO 7
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 7
tgcaagaatt caagccatc                                                      19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcagcaggtt ccaagtaatg                                                     20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gctgtccttt ccctgtatgc                                                     20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acgaccagca agatccaaac                                                     20

<210> SEQ ID NO 11
<211> LENGTH: 288
<212> TYPE: PRT
<213> ORGANISM: Vitis vinifera

<400> SEQUENCE: 11

Met Asp Thr Ala Gln Trp Pro Gln Glu Ile Val Val Lys Pro Leu Glu
1               5                   10                  15

Glu Ile Val Thr Asn Thr Cys Pro Lys Pro Ala Leu Glu Lys Arg Ala
            20                  25                  30

Arg Pro Gln Lys Glu Gln Ala Leu Asn Cys Pro Arg Cys Asn Ser Thr
        35                  40                  45

Asn Thr Lys Phe Cys Tyr Tyr Asn Asn Tyr Ser Leu Ser Gln Pro Arg
    50                  55                  60

Tyr Phe Cys Lys Ala Cys Arg Arg Tyr Trp Thr Glu Gly Gly Ser Leu
65                  70                  75                  80

Arg Asn Ile Pro Val Gly Gly Gly Ser Arg Lys Asn Lys Arg Ser Ser
                85                  90                  95

Ser Ser Ser Ser Ser Ser Ser Ser Ala Ser Ser Lys Lys Leu Pro
            100                 105                 110

Asp Leu Val Pro Pro Gly Cys Ser Gln Ser Ser Ala Gln Asn Pro Lys
        115                 120                 125
```

```
Ile His Glu Gly Gln Asp Leu Asn Leu Ser Phe Pro Ala Ala Gln Asp
            130                 135                 140

Phe Arg Ser Val Ser Glu Phe Met Gln Met Pro Ser Ile Glu Asn Ser
145                 150                 155                 160

Asn Asn Asn Thr Asn Asn Ser Ser Lys Ser His Ile Thr Ser Thr Ser
                165                 170                 175

Ser Thr Ser Ser His Leu Ser Ala Leu Glu Leu Leu Thr Gly Ile Thr
            180                 185                 190

Ser Arg Gly Leu Asn Ser Phe Met Pro Met Pro Ile Pro Asp Pro Asn
            195                 200                 205

Thr Val Tyr Thr Thr Gly Phe Pro Met Gln Glu Phe Lys Pro Thr Leu
    210                 215                 220

Asn Phe Ser Leu Asp Gly Leu Gly Ser Gly Tyr Gly Ser Ile Gln Gly
225                 230                 235                 240

Val Gln Gly Ser Ser Ser Gly Arg Leu Leu Phe Pro Phe Glu Asp Leu
                245                 250                 255

Lys Gln Val Ser Ser Thr Ala Asp His Ile Glu Gln Thr Arg Glu Gln
            260                 265                 270

Gly Asp Ser Thr Gly Tyr Trp Thr Gly Met Leu Gly Gly Ser Trp
            275                 280                 285

<210> SEQ ID NO 12
<211> LENGTH: 287
<212> TYPE: PRT
<213> ORGANISM: Gossypium sp.

<400> SEQUENCE: 12

Met Asp Thr Ala Gln Trp Pro Gln Glu Ile Val Val Lys Pro Ile Glu
1               5                   10                  15

Glu Ile Val Thr Asn Thr Cys Pro Lys Pro Thr Gly Leu Glu Arg Lys
            20                  25                  30

Ile Arg Pro Gln Lys Glu Gln Ala Leu Asn Cys Pro Arg Cys Asn Ser
        35                  40                  45

Thr Asn Thr Lys Phe Cys Tyr Tyr Asn Asn Tyr Ser Leu Thr Gln Pro
    50                  55                  60

Arg Tyr Phe Cys Lys Thr Cys Arg Arg Tyr Trp Thr Glu Gly Gly Ser
65                  70                  75                  80

Leu Arg Asn Ile Pro Val Gly Gly Gly Ser Arg Lys Asn Lys Arg Ser
                85                  90                  95

Ser Thr Ser Ser Ser Ser Ile Ser Thr Ser Leu Thr Ser Ser Lys
            100                 105                 110

Lys Leu Pro Gly Leu Val Thr Pro Ser Leu Ser Gln Cys Ser Thr
        115                 120                 125

Gln Asn Pro Lys Ile His Asp Gly Gln Asp Leu Asn Leu Ala Phe Pro
    130                 135                 140

Thr Ala Ser Gln Gly Tyr Arg Ser Leu Ser Glu Leu Val Gln Leu Pro
145                 150                 155                 160

Leu Glu Asn Asn Asn Lys Asn Gln Ile Pro Ser Ser Ser Ser Ser Ser
                165                 170                 175

Pro Thr Thr Ser Gln Leu Ser Ala Leu Glu Leu Leu Thr Gly Ile Thr
            180                 185                 190

Ser Arg Gly Phe Asn Ser Phe Ile Pro Met Pro Val Pro Asp Pro Asn
            195                 200                 205

Thr Val Tyr Thr Pro Gly Asn Phe Pro Met Gln Asp Phe Lys Pro Thr
```

```
            210                 215                 220
Leu Asn Phe Ser Leu Asp Gly Leu Gly Asn Gly Tyr Gly Ser Leu His
225                 230                 235                 240

Gly Val Gln Glu Thr Thr Gly Arg Leu Leu Phe Pro Phe Glu Asp Leu
                245                 250                 255

Lys Gln Val Ser Thr Thr Thr Asp Ile Asp Gln His Lys Asp Gln Gly
                260                 265                 270

Asp Ser Thr Gly Tyr Trp Thr Gly Met Leu Gly Gly Ser Trp
                275                 280                 285

<210> SEQ ID NO 13
<211> LENGTH: 304
<212> TYPE: PRT
<213> ORGANISM: Eucalyptus sp.

<400> SEQUENCE: 13

Met Asp Thr Ala Gln Trp Pro Gln Glu Ile Val Val Lys Pro Ile Glu
1               5                   10                  15

Asp Ile Val Thr Ser Thr Cys Thr Ala Ala Thr Pro Lys Pro Ser
                20                  25                  30

Ser Ser Ser Val Ser Glu Arg Lys Pro Arg Pro Gln Lys Glu Gln Ala
            35                  40                  45

Leu Asn Cys Pro Arg Cys Asn Ser Thr Asn Thr Lys Phe Cys Tyr Tyr
50                  55                  60

Asn Asn Tyr Ser Leu Thr Gln Pro Arg Tyr Phe Cys Lys Thr Cys Arg
65                  70                  75                  80

Arg Tyr Trp Thr Asp Gly Gly Ser Leu Arg Asn Ile Pro Val Gly Gly
                85                  90                  95

Gly Ser Arg Lys Asn Lys Arg Ser Ser Ser Ala Ser Ser Ser Ser
            100                 105                 110

Ser Ser Phe Asn Ser Ser Ser Lys Lys Leu Pro Asp Leu Ile Ser Thr
            115                 120                 125

Pro Ala Ser Asn Pro Asn Asn Lys Val Thr Leu His Glu Gly Gln Asp
            130                 135                 140

Leu Asn Leu Ala Phe Pro Asn Pro His His Asp Phe Lys Ser Ile
145                 150                 155                 160

Ser Glu Leu Val Gln Val Pro Ser Leu Glu Ala Ser Lys Asn His His
                165                 170                 175

Ile Ser Ala Asn Ser Ser Ala Gly Ala Ser Met Ala Pro Pro Gln
            180                 185                 190

Leu Ser Ala Leu Glu Leu Leu Ser Gly Ile Thr Ser Arg Gly Ser Phe
            195                 200                 205

Ser Ser Phe Met Ser Met Pro Val His Asp Pro Gly Ser Val Tyr Thr
            210                 215                 220

Pro Gly Leu Phe Ala Leu Pro Asp Phe Lys Pro Thr Leu Asn Phe Ser
225                 230                 235                 240

Leu Asp Gly Leu Gly Ser Gly Gly Tyr Arg Ser Leu Pro Ser Val Gln
                245                 250                 255

Glu Gly Gly Thr Asn Gly Gly Arg Leu Leu Phe Pro Phe Glu Asp Leu
            260                 265                 270

Lys Pro Val Ser Ser Thr Ser Asp Met Glu Gln Asn Arg Gly Asp Gln
            275                 280                 285

Gly Asp Ser Asp Gly Tyr Trp Ser Gly Met Leu Gly Gly Gly Ser Trp
            290                 295                 300
```

<210> SEQ ID NO 14
<211> LENGTH: 287
<212> TYPE: PRT
<213> ORGANISM: Vitis vinifera

<400> SEQUENCE: 14

```
Met Asp Thr Ala Gln Trp Pro Gln Gly Ile Gly Val Val Lys Pro Met
1               5                   10                  15

Glu Ser Ser Gly Pro Val Ala Glu Arg Arg Ala Arg Pro Gln Lys Asp
            20                  25                  30

Gln Ala Leu Asn Cys Pro Arg Cys Asn Ser Thr Asn Thr Lys Phe Cys
        35                  40                  45

Tyr Tyr Asn Asn Tyr Ser Leu Ser Gln Pro Arg Tyr Phe Cys Lys Thr
    50                  55                  60

Cys Arg Arg Tyr Trp Thr Glu Gly Gly Ser Leu Arg Asn Val Pro Val
65                  70                  75                  80

Gly Gly Gly Ser Arg Lys Asn Lys Arg Ser Thr Ser Ser Ser Ser Ser
                85                  90                  95

Ser Ser Ser Pro Ala Ser Ser Lys Lys Leu Leu Pro Asp His Leu Ile
            100                 105                 110

Thr Ser Thr Pro Pro Gly Phe Pro Ser Ser Ala Ser Gln Asn Pro Lys
        115                 120                 125

Ile His Glu Gly Gln Asp Leu Asn Leu Ala Phe Pro Pro Pro Glu
    130                 135                 140

Asp Tyr Asn Asn Ser Ile Ser Glu Phe Ala Asp Leu Ser Tyr Asn Gly
145                 150                 155                 160

Asp Ser Lys Pro His Leu Gln Asn Pro Thr Pro Ser Ser Ser Ser
            165                 170                 175

His His His Leu Ser Ala Met Glu Leu Leu Lys Ser Thr Gly Ile Ala
        180                 185                 190

Ser Arg Gly Leu Gly Ser Phe Met Pro Met Ser Val Ser Asp Ser Asn
    195                 200                 205

Ser Ile Tyr Ser Ser Gly Phe Pro Leu Gln Glu Phe Lys Pro Thr Leu
    210                 215                 220

Asn Phe Ser Leu Asp Gly Phe Gln Ser Gly Tyr Gly Ser Leu Gln Gly
225                 230                 235                 240

Val Gln Glu Ser Gly Ala Arg Leu Leu Phe Pro Leu Glu Asp Leu Lys
            245                 250                 255

Gln Val Ser Asn Thr Thr Glu Phe Glu Gln Ser Arg Gly Val Gln Gly
        260                 265                 270

Asp Ser Ala Gly Tyr Trp Asn Gly Met Leu Gly Gly Ser Trp
    275                 280                 285
```

<210> SEQ ID NO 15
<211> LENGTH: 297
<212> TYPE: PRT
<213> ORGANISM: Populus trichocarpa

<400> SEQUENCE: 15

```
Met Asp Thr Ala Thr Gln Trp Ala Gln Gly Ile Gly Ala Val Asn Pro
1               5                   10                  15

Met Glu Gly Ser Arg Pro Asp Val Leu Glu Arg Arg Ala Arg Ala Gln
            20                  25                  30

Lys Asp Gln Ala Leu Asn Cys Pro Arg Cys Asn Ser Thr Asn Thr Lys
        35                  40                  45
```

```
Phe Cys Tyr Tyr Asn Asn Tyr Ser Leu Ser Gln Pro Arg Tyr Phe Cys
 50                  55                  60

Lys Thr Cys Arg Arg Tyr Trp Thr Ala Gly Gly Ser Leu Arg Asn Val
 65                  70                  75                  80

Pro Val Gly Gly Gly Ser Arg Lys Asn Lys Arg Ser Ser Ser Thr Ala
                 85                  90                  95

Ser Thr Ser Ala Ala Gly Ala Ala Ser Lys Lys Phe Pro Leu Asp
                100                 105                 110

Leu Thr Gln Pro Asn Leu Pro His Ser Ala Ser Gln Asn Pro Lys Ile
                115                 120                 125

His Glu Gly Gln Asp Leu Asn Leu Ala Tyr Pro Pro Ser Ala Asp Asp
130                 135                 140

Tyr Ser Asn Leu Ser Glu Phe Val Glu Ile Pro Phe Asp Thr Glu Ser
145                 150                 155                 160

Asn Lys Thr His His Gln Asn Pro Asn Pro Ser Ser Thr Ser Pro Ser
                165                 170                 175

His His His His His His Val Ser Pro Met Glu Phe Leu Lys Ser Thr
                180                 185                 190

Ala Met Asn Ser Arg Gly Phe Ser Ala Phe Met Ser Ile Pro Pro Leu
                195                 200                 205

Ser Asp Ser Asn Asn Thr Met Phe Ser Thr Gly Phe Pro Leu Gln Glu
210                 215                 220

Phe Lys Ser Thr Gln Asn Phe Ser Leu Glu Gly Leu Glu Ser Gly Tyr
225                 230                 235                 240

Ser Asn Thr Gln Gly Val His Glu Thr Cys Gly Ser Ala Arg Leu Leu
                245                 250                 255

Phe Pro Ile Glu Asp Leu Lys Gln Gln Val Pro Ser Asn Thr Glu Phe
                260                 265                 270

Glu Gln Asn Thr Arg Glu Gln Arg Asp Asn Ala Pro Val Gly Tyr Trp
                275                 280                 285

Asn Gly Met Leu Gly Gly Gly Ser Trp
                290                 295

<210> SEQ ID NO 16
<211> LENGTH: 297
<212> TYPE: PRT
<213> ORGANISM: Glycine max

<400> SEQUENCE: 16

Met Asp Thr Ala Gln Trp Ala Gln Gly Ile Gly Val Val Lys Gln Pro
  1               5                  10                  15

Met Glu Gly Ser Lys Pro Pro Pro Pro Pro Pro Met Leu Glu
                 20                  25                  30

Arg Arg Ala Arg Pro Gln Lys Asp Gln Ala Leu Asn Cys Pro Arg Cys
                 35                  40                  45

Asn Ser Thr Asn Thr Lys Phe Cys Tyr Tyr Asn Asn Tyr Ser Leu Ser
 50                  55                  60

Gln Pro Arg Tyr Phe Cys Lys Thr Cys Arg Arg Tyr Trp Thr Glu Gly
 65                  70                  75                  80

Gly Ser Leu Arg Asn Val Pro Val Gly Gly Ser Arg Lys Asn Lys
                 85                  90                  95

Arg Ser Thr Pro Pro Ala Pro Pro Ser Ala Pro Ala Pro Thr Lys Lys
                100                 105                 110

Leu Ser Asp Leu Ala Thr Pro Asn Phe Pro Gln Ser Ala Ser Gln Asp
                115                 120                 125
```

```
Pro Lys Ile His Gln Gly Gln Asp Leu Asn Leu Ala Tyr Pro Ala
    130                 135                 140

Glu Asp Tyr Ser Thr Val Ser Lys Phe Ile Glu Val Pro Tyr Ser Thr
145                 150                 155                 160

Glu Leu Asp Lys Gly Thr Thr Gly Leu His Gln Asn Pro Thr Ser Ser
                165                 170                 175

Ser Thr Thr Thr Ser Ala Ser Ser Gln Leu Ser Ala Met Glu Leu Leu
            180                 185                 190

Lys Thr Gly Ile Ala Ala Ala Ser Ser Arg Gly Leu Asn Ser Phe Met
        195                 200                 205

Pro Met Tyr Asn Ser Thr His Gly Phe Pro Leu Gln Asp Phe Lys Pro
    210                 215                 220

Pro His Gly Leu Asn Phe Ser Leu Glu Gly Phe Glu Asn Gly Tyr Gly
225                 230                 235                 240

Gly Leu Gln Gly Ile Gln Glu Gly Pro Thr Gly Gly Ala Arg Ile Leu
                245                 250                 255

Phe Pro Thr Val Glu Asp Leu Lys Gln Gln Val Pro Ser Thr Asn Glu
            260                 265                 270

Phe Asp Gln Gln Asn Arg Ser Gln Glu Gly Ser Ala His Gly Tyr Trp
        275                 280                 285

Asn Gly Met Leu Gly Gly Gly Ser Trp
    290                 295

<210> SEQ ID NO 17
<211> LENGTH: 306
<212> TYPE: PRT
<213> ORGANISM: Glycine max

<400> SEQUENCE: 17

Met Asp Thr Ala Gln Trp Ala Gln Gly Ile Gly Val Val Lys Gln Pro
1               5                   10                  15

Thr Met Glu Gly Gly Ser Lys Pro Pro Pro Pro Met Leu Glu Arg
            20                  25                  30

Arg Ala Arg Pro Gln Lys Asp Gln Ala Leu Asn Cys Pro Arg Cys Asn
        35                  40                  45

Ser Thr Asn Thr Lys Phe Cys Tyr Tyr Asn Asn Tyr Ser Leu Ser Gln
    50                  55                  60

Pro Arg Tyr Phe Cys Lys Thr Cys Arg Arg Tyr Trp Thr Glu Gly Gly
65                  70                  75                  80

Ser Leu Arg Asn Val Pro Val Gly Gly Gly Ser Arg Lys Asn Lys Arg
                85                  90                  95

Ser Thr Pro Ser Ala Pro Pro Ser Ser Ala Ser Ala Gln Ala Lys
            100                 105                 110

Lys Leu Pro Asp Leu Thr Thr Pro Asn Phe Pro Gln Ser Ala Ser Gln
        115                 120                 125

Asp Pro Lys Ile His Gln Gly Gln Asp Leu Asn Leu Ala Tyr Pro Pro
    130                 135                 140

Ala Glu Asp Tyr Asn Thr Val Ser Met Ser Lys Leu Ile Glu Val Pro
145                 150                 155                 160

Tyr Asn Thr Glu Leu Asp Lys Gly Gly Leu His Gln Asn Pro Thr Ser
                165                 170                 175

Ser Ser Thr Pro Thr Ser Ala Ser Ser His His Gln Leu Ser Ala Met
            180                 185                 190

Glu Leu Leu Lys Thr Gly Ile Ala Ala Ala Ser Ser Arg Gly Leu Asn
```

```
                195                 200                 205
Ser Phe Met Pro Met Tyr Asn Ser Thr His His Gly Phe Pro Leu Gln
210                 215                 220

Asp Phe Lys Pro Pro His His Gly Leu Asn Phe Ser Leu Glu Gly Phe
225                 230                 235                 240

Asp Asn Gly Thr Tyr Gly Gly Leu His Gln Gly Ile Gln Glu Asp Pro
                245                 250                 255

Thr Thr Gly Gly Ala Arg Ile Leu Phe Pro Thr Val Glu Asp Leu Lys
                260                 265                 270

Gln Gln Val Pro Ser Thr Asn Glu Phe Asp His Gln Gln Asn Arg Ser
            275                 280                 285

Gln Glu Gly Ser Ala His Gly Tyr Trp Asn Gly Met Leu Gly Gly Gly
        290                 295                 300

Ser Trp
305

<210> SEQ ID NO 18
<211> LENGTH: 362
<212> TYPE: PRT
<213> ORGANISM: Sorghum bicolor

<400> SEQUENCE: 18

Met Glu Glu Met Leu Met Ala Gly Asn Ala Asn Pro Asn Gln Asn Pro
1               5                   10                  15

Asn Pro Pro Pro Ala Pro Ser Ala Pro Gly Ala Gln Arg Ala Gly
            20                  25                  30

Ala Pro Ala Ala Gly Ala Ala Ala Pro Ser Ala Gly Ala Thr Gly
        35                  40                  45

Gly Pro Ala Gly Ala Gly Thr Glu Arg Arg Ala Arg Pro Gln Lys Glu
    50                  55                  60

Lys Ala Leu Asn Cys Pro Arg Cys Asn Ser Thr Asn Thr Lys Phe Cys
65                  70                  75                  80

Tyr Tyr Asn Asn Tyr Ser Leu Gln Gln Pro Arg Tyr Phe Cys Lys Thr
                85                  90                  95

Cys Arg Arg Tyr Trp Thr Glu Gly Gly Ser Leu Arg Asn Val Pro Val
            100                 105                 110

Gly Gly Gly Ser Arg Lys Asn Lys Arg Ser Ser Ser Ala Val Ser Ser
        115                 120                 125

Ala Ala Ala Ala Ser Thr Ser Ala Ala Met Ser Gly Thr Val Ser Val
130                 135                 140

Gly Leu Pro Ala Lys Asn Pro Lys Leu Met His Glu Gly Ala His Asp
145                 150                 155                 160

Leu Asn Leu Ala Phe Pro His His Asn Gly Arg Ala Leu Gln Pro Pro
                165                 170                 175

Glu Phe Pro Ala Phe Pro Ser Leu Glu Ser Ser Ser Val Cys Asn Pro
            180                 185                 190

Gly Ala Ala Gly Met Val Gly Asn Gly Ala Ala Gly Arg Gly Met Gly
        195                 200                 205

Ala Leu Ser Ala Met Glu Leu Leu Arg Ser Thr Gly Cys Tyr Val Pro
    210                 215                 220

Leu Gln His Val Gln Leu Gly Met Pro Ala Glu Tyr Ala Ala Ala Gly
225                 230                 235                 240

Phe Ala Leu Gly Glu Phe Arg Met Pro Pro Pro Gln Ser His Ser
                245                 250                 255
```

-continued

```
Val Leu Gly Phe Ser Leu Asp Thr His Gly Thr Gly Val Gly
            260                 265                 270

Ala Gly Gly Tyr Ser Ala Gly Leu Gln Asp Ser Ala Ala Gly Arg Leu
        275                 280                 285

Leu Phe Pro Phe Glu Asp Leu Lys Pro Ala Val Ser Ala Ala Ala Gly
    290                 295                 300

Gly Gly Gly Ala Ser Asn Gly Ala Asp His His Gln Tyr Glu His Ser
305                 310                 315                 320

Lys Asp Gln Ala Ala Gly Asp Gly Gly Ser Gly Pro Ser Gly Val Thr
                325                 330                 335

Gly Gly His Glu Thr Pro Gly Phe Trp Ser Asn Ser Leu Ile Gly Asn
            340                 345                 350

Gly Ser Ser Asn Gly Gly Gly Pro Trp
        355                 360
```

<210> SEQ ID NO 19
<211> LENGTH: 376
<212> TYPE: PRT
<213> ORGANISM: Zea mays

<400> SEQUENCE: 19

```
Met Asp Ala Ala Gln Trp His Gln His Gln Gly Leu Gly Leu Gly Lys
1               5                   10                  15

Pro Met Glu Glu Met Leu Met Ala Gly Asn Ala Asn Leu Asn Gln Asn
            20                  25                  30

Pro Asn Pro Pro Ala Ala Pro Ser Ala Pro Gly Ala Gln Arg Ala
        35                  40                  45

Gly Ala Pro Ala Ala Val Ala Ala Pro Pro Ser Ala Gly Ala Thr
50                  55                  60

Gly Gly Ala Gly Pro Glu Arg Arg Ala Arg Pro Gln Lys Glu Lys Ala
65                  70                  75                  80

Leu Asn Cys Pro Arg Cys Asn Ser Thr Asn Thr Lys Phe Cys Tyr Tyr
                85                  90                  95

Asn Asn Tyr Ser Leu Gln Gln Pro Arg Tyr Phe Cys Lys Thr Cys Arg
            100                 105                 110

Arg Tyr Trp Thr Glu Gly Gly Ser Leu Arg Asn Val Pro Val Gly Gly
        115                 120                 125

Gly Ser Arg Lys Asn Lys Arg Ser Ser Ser Ala Val Ser Ser Ala Ala
    130                 135                 140

Ala Ala Ala Ala Ala Ser Thr Ser Ala Ala Met Ser Gly Thr Val Pro
145                 150                 155                 160

Val Gly Leu Ala Ala Lys Asn Pro Lys Leu Met His Glu Gly Ala His
                165                 170                 175

Asp Leu Asn Leu Ala Phe Pro His His Asn Gly Arg Ala Leu Gln Pro
            180                 185                 190

Pro Glu Phe Pro Ala Phe Pro Ser Leu Glu Ser Ser Ser Val Cys Asn
        195                 200                 205

Pro Gly Ala Ala Met Leu Gly Asn Gly Ala Ala Gly Arg Gly Met Gly
    210                 215                 220

Ala Leu Ser Gly Leu Glu Leu Leu Arg Ser Thr Gly Cys Tyr Val Pro
225                 230                 235                 240

Leu Gln His Phe Gln Leu Gly Met Pro Ala Glu Tyr Ala Ala Ala Gly
                245                 250                 255

Phe Ser Leu Gly Glu Phe Arg Val Pro Pro Pro Gln Ser Gln Ser
            260                 265                 270
```

```
Val Phe Gly Phe Ser Leu Asp Thr His Gly Thr Gly Gly Val Gly Gly
            275                 280                 285

Ala Gly Gly Tyr Ser Ala Gly Leu Gln Glu Ser Ala Ala Gly Arg Met
        290                 295                 300

Leu Phe Pro Phe Glu Asp Leu Lys Pro Ala Val Ser Ala Ala Gly Gly
305                 310                 315                 320

Gly Ala Ser Asn Gly Ala Asp His His His Tyr Glu His Ser Lys Asp
                325                 330                 335

Gln Ala Ala Gly Asp Gly Gly Ala Ser Gly Val Thr Gly Gly His
                340                 345                 350

Glu Ala Pro Ala Gly Phe Trp Ser Asn Ser Met Ile Gly Asn Gly Ser
                355                 360                 365

Ser Asn Gly Gly Gly Gly Ser Trp
        370                 375

<210> SEQ ID NO 20
<211> LENGTH: 381
<212> TYPE: PRT
<213> ORGANISM: Oryza sativa

<400> SEQUENCE: 20

Met Asp Ala Ala His Trp His Gln Gly Leu Gly Leu Val Lys Pro Met
1               5                   10                  15

Glu Glu Met Leu Met Gly Ala Asn Pro Asn Pro Asn Gly Ser Ser Asn
            20                  25                  30

Gln Pro Pro Pro Pro Ser Ser Ala Ala Ser Ala Gln Arg Pro Ile
        35                  40                  45

Ala Pro Pro Ala Ala Gly Ala Ala Gly Ala Gly Ala Ala Gly Ala
50                  55                  60

Gly Ala Gly Thr Glu Arg Arg Ala Arg Pro Gln Lys Glu Lys Ala Leu
65                  70                  75                  80

Asn Cys Pro Arg Cys Asn Ser Thr Asn Thr Lys Phe Cys Tyr Tyr Asn
                85                  90                  95

Asn Tyr Ser Leu Gln Gln Pro Arg Tyr Phe Cys Lys Thr Cys Arg Arg
            100                 105                 110

Tyr Trp Thr Glu Gly Gly Ser Leu Arg Asn Val Pro Val Gly Gly Gly
        115                 120                 125

Ser Arg Lys Asn Lys Arg Ser Ser Ser Val Val Pro Ser Ala Ala
            130                 135                 140

Ala Ser Ala Ser Thr Ser Ala Ala Val Ser Gly Ser Val Pro Val Gly
145                 150                 155                 160

Leu Ala Ala Lys Asn Pro Lys Leu Met His Glu Gly Ala Gln Asp Leu
                165                 170                 175

Asn Leu Ala Phe Pro His His His Gly Arg Ala Leu Gln Pro Pro Glu
            180                 185                 190

Phe Thr Ala Phe Pro Ser Leu Glu Ser Ser Val Cys Asn Pro Gly
        195                 200                 205

Gly Asn Leu Ala Ala Ala Asn Gly Ala Gly Arg Gly Ser Val Gly
    210                 215                 220

Ala Phe Ser Ala Met Glu Leu Leu Arg Ser Thr Gly Cys Tyr Val Pro
225                 230                 235                 240

Leu Pro Gln Met Ala Pro Leu Gly Met Pro Ala Glu Tyr Ala Ala Ala
                245                 250                 255

Gly Phe His Leu Gly Glu Phe Arg Met Pro Pro Pro Pro Gln Gln Gln
```

```
                    260                 265                 270
Gln Gln Gln Gln Ala Gln Thr Val Leu Gly Phe Ser Leu Asp Thr His
            275                 280                 285

Gly Ala Gly Ala Gly Gly Ser Gly Val Phe Gly Ala Cys Ser Ala
        290                 295                 300

Gly Leu Gln Glu Ser Ala Ala Gly Arg Leu Leu Phe Pro Phe Glu Asp
305                 310                 315                 320

Leu Lys Pro Val Val Ser Ala Ala Gly Asp Ala Asn Ser Gly Gly
                    325                 330                 335

Asp His Gln Tyr Asp His Gly Lys Asn Gln Gly Gly Gly Gly Val
            340                 345                 350

Ile Gly Gly His Glu Ala Pro Gly Phe Trp Asn Ser Ser Met Ile Gly
        355                 360                 365

Asn Gly Ser Ser Asn Gly Gly Gly Gly Ser Trp
    370                 375                 380

<210> SEQ ID NO 21
<211> LENGTH: 356
<212> TYPE: PRT
<213> ORGANISM: Sorghum bicolor

<400> SEQUENCE: 21

Met Glu Glu Met Leu Met Ala Ala Asn Ala Gly Ala Ala Asn Pro Ser
1               5                   10                  15

Gln Gly Ser Asn Asn Pro Asn Pro Ala Pro Ala Pro Gly Gly Ala
            20                  25                  30

Leu Arg Gly Gly Gly Ala Pro Ala Ala Pro Leu Ala Gly Ala Gly Ser
        35                  40                  45

Thr Glu Arg Arg Ala Arg Pro Gln Lys Glu Lys Ala Leu Asn Cys Pro
    50                  55                  60

Arg Cys Asn Ser Thr Asn Thr Lys Phe Cys Tyr Tyr Asn Asn Tyr Ser
65                  70                  75                  80

Leu Gln Gln Pro Arg Tyr Phe Cys Lys Thr Cys Arg Arg Tyr Trp Thr
                85                  90                  95

Glu Gly Gly Ser Leu Arg Asn Val Pro Val Gly Gly Gly Ser Arg Lys
            100                 105                 110

Asn Lys Arg Ser Ser Ser Ser Ala Ser Ala Ser Ala Ser Thr Ser Ala
        115                 120                 125

Ser Val Thr Ser Ser Ser Met Ala Ser Ala Glu Gly Ala Ala Ala Ser
    130                 135                 140

Lys Asn Pro Lys Leu Ala His Glu Gly Ala His Asp Leu Asn Leu Ala
145                 150                 155                 160

Phe Pro His His Gly Gly Leu His Ala Pro Glu Phe Ala Ala Phe Pro
                165                 170                 175

Ser Leu Glu Ser Ser Asn Val Cys Asn Pro Gly Gly Gly Met Thr Ser
            180                 185                 190

Asn Gly Arg Gly Gly Gly Ala Gly Pro Ala Val Gly Ala Leu Ser Ala
        195                 200                 205

Met Glu Leu Leu Arg Ser Ser Gly Cys Tyr Met Pro Leu Gln Met Pro
    210                 215                 220

Met Gln Met Gln Gly Asp Tyr Thr Ala Ala Glu Phe Ala Leu Gly Asp
225                 230                 235                 240

Phe Arg Thr Pro Pro Pro Pro Ser Gln Ser Val Leu Gly Phe Ser
                245                 250                 255
```

```
Leu Asp Ala His Gly Pro Gly Ser Gly Ala Ala Ala Gly Tyr Gly
            260                 265                 270

Ser Ser Ala Gly Leu Gln Gly Val Thr Glu Asn Ala Gly Arg Leu Leu
            275                 280                 285

Phe Pro Phe Glu Asp Leu Lys Pro Pro Val Ser Ser Gly Gly Gly
290                 295                 300

Val Ala Gly Gly Ala Thr Gly Ala Gly Asp Gly Asn Ser Asn His
305                 310                 315                 320

Asn Gln Phe Asp His Asn Lys Glu Gln Asp Gly Gly Gly Pro Gly
                325                 330                 335

Ala Gly His Asp Thr Pro Gly Phe Trp Ser Gly Met Ile Gly Gly Ser
            340                 345                 350

Gly Ala Ser Trp
            355

<210> SEQ ID NO 22
<211> LENGTH: 370
<212> TYPE: PRT
<213> ORGANISM: Zea mays

<400> SEQUENCE: 22

Met Asp Ala Ala His Trp Gln Gln Gly Leu Gly Leu Val Lys Pro Met
1               5                   10                  15

Glu Glu Met Leu Met Ala Ala Asn Ala Gly Ala Ala Asn Pro Ser Gln
            20                  25                  30

Ser Ser Asn Pro Asn Pro Pro Ala Pro Ala Pro Ser Leu Ala Pro Gly
        35                  40                  45

Gly Leu Leu Gly Gly Gly Ala Pro Ala Pro Leu Ala Gly Ala Gly Ser
    50                  55                  60

Thr Glu Arg Arg Ala Arg Pro Gln Lys Glu Lys Ala Leu Asn Cys Pro
65                  70                  75                  80

Arg Cys Asn Ser Thr Asn Thr Lys Phe Cys Tyr Tyr Asn Asn Tyr Ser
                85                  90                  95

Leu Gln Gln Pro Arg Tyr Phe Cys Lys Thr Cys Arg Arg Tyr Trp Thr
            100                 105                 110

Glu Gly Gly Ser Leu Arg Asn Val Pro Val Gly Gly Gly Ser Arg Lys
        115                 120                 125

Asn Lys Arg Ser Ser Ser Ala Ser Ala Ser Ala Ser Thr Ser Gly
    130                 135                 140

Ser Val Thr Ser Ser Ser Met Ala Ser Thr Ala Gly Ala Gly Ser Lys
145                 150                 155                 160

Asn Pro Lys Leu Ala His Glu Gly Ala His Asp Leu Asn Leu Ala Phe
                165                 170                 175

Pro His His Gly Gly Leu His Ala Pro Glu Phe Ala Ala Phe Pro Ser
            180                 185                 190

Leu Glu Ser Ser Asn Val Cys Asn Pro Gly Gly Gly Met Thr Ser Asn
        195                 200                 205

Gly Arg Gly Gly Gly Ala Gly Pro Ala Val Gly Ala Leu Ser Ala Met
    210                 215                 220

Glu Leu Leu Arg Ser Ser Gly Cys Tyr Met Pro Leu Gln Met Pro Met
225                 230                 235                 240

Pro Met Ala Met Pro Gly Asp Tyr Thr Ala Ala Gly Phe Ala Leu Gly
                245                 250                 255

Glu Tyr Arg Thr Pro Pro Pro Pro Ser Gln Ser Val Leu Gly Phe
            260                 265                 270
```

-continued

Ser Leu Asp Ala His Gly Pro Gly Ser Gly Ala Thr Ala Ala Gly Tyr
        275                 280                 285

Gly Ser Ser Ala Gly Leu Gln Gly Val Pro Glu Asn Ala Gly Arg Leu
    290                 295                 300

Leu Phe Pro Phe Glu Asp Leu Lys Pro Pro Val Gly Ser Glu Gly Gly
305                 310                 315                 320

Gly Gly Ala Thr Gly Ala Ser Asp Gly Asn Ser Ser His Thr Gln
                325                 330                 335

Phe Asp His Asn Asn Lys Glu Gln Gly Gly Gly Thr Gly Ala Gly
                340                 345                 350

His Asp Thr Pro Gly Phe Trp Ser Gly Met Ile Gly Gly Ser Gly Ala
                355                 360                 365

Ser Trp
    370

<210> SEQ ID NO 23
<211> LENGTH: 378
<212> TYPE: PRT
<213> ORGANISM: Oryza sativa

<400> SEQUENCE: 23

Met Asp Ala Ala His Trp His Gln Gly Leu Gly Leu Val Lys Pro Met
1               5                   10                  15

Glu Glu Met Leu Met Ala Ala Asn Ala Ala Gly Ala Asn Pro Asn
                20                  25                  30

Pro Ala Ala Thr Ala Pro Ser Ser Val Thr Gly Gly Ala Leu Arg Gly
                35                  40                  45

Gly Gly Gly Gly Gly Ala Pro Pro Val Ala Gly Ala Gly Ala Gly
    50                  55                  60

Ser Thr Glu Arg Arg Ala Arg Pro Gln Lys Glu Lys Ala Leu Asn Cys
65              70                  75                  80

Pro Arg Cys Asn Ser Thr Asn Thr Lys Phe Cys Tyr Tyr Asn Asn Tyr
                85                  90                  95

Ser Leu Gln Gln Pro Arg Tyr Phe Cys Lys Thr Cys Arg Arg Tyr Trp
                100                 105                 110

Thr Glu Gly Gly Ser Leu Arg Asn Val Pro Val Gly Gly Gly Ser Arg
                115                 120                 125

Lys Asn Lys Arg Ser Ser Ser Ala Ala Ser Ala Ser Pro Ala Ser
    130                 135                 140

Ala Ser Thr Ala Asn Ser Val Val Thr Ser Ala Ser Met Ser Met Ser
145                 150                 155                 160

Met Ala Ser Thr Gly Gly Gly Ala Ser Lys Asn Pro Lys Leu Val His
                165                 170                 175

Glu Gly Ala Gln Asp Leu Asn Leu Ala Phe Pro His His Gly Gly Leu
                180                 185                 190

Gln Ala Pro Gly Glu Phe Pro Ala Phe Pro Ser Leu Glu Ser Ser Ser
        195                 200                 205

Val Cys Asn Pro Gly Gly Pro Met Gly Thr Asn Gly Arg Gly Gly Gly
    210                 215                 220

Ala Leu Ser Ala Met Glu Leu Leu Arg Ser Thr Gly Cys Tyr Met Pro
225                 230                 235                 240

Leu Gln Val Pro Met Gln Met Pro Ala Glu Tyr Ala Thr Pro Gly Phe
                245                 250                 255

Ala Leu Gly Glu Phe Arg Ala Pro Pro Pro Pro Gln Ser Ser Gln

```
                    260                 265                 270
Ser Leu Leu Gly Phe Ser Leu Asp Ala His Gly Ser Val Gly Gly Pro
            275                 280                 285

Ser Ala Ala Gly Phe Gly Ser Ser Ala Gly Leu Gln Gly Val Pro Glu
            290                 295                 300

Ser Thr Gly Arg Leu Leu Phe Pro Phe Glu Asp Leu Lys Pro Thr Val
305                 310                 315                 320

Ser Ser Gly Thr Gly Gly Gly Ala Ser Gly Gly Gly Ala Gly Val
                325                 330                 335

Asp Gly Gly His Gln Phe Asp His Gly Lys Glu Gln Gln Ala Gly Gly
            340                 345                 350

Gly Gly Gly Gly Pro Gly Gly His Asp Thr Pro Gly Phe Trp Asn Gly
            355                 360                 365

Met Ile Gly Gly Gly Ser Gly Thr Ser Trp
        370                 375

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      WALLDOF motif consensus sequence
<220> FEATURE:
<221> NAME/KEY: MOD_RES
<222> LOCATION: (2)..(2)
<223> OTHER INFORMATION: Pro or Ala
<220> FEATURE:
<221> NAME/KEY: MOD_RES
<222> LOCATION: (5)..(5)
<223> OTHER INFORMATION: Asp or Glu
<220> FEATURE:
<221> NAME/KEY: MOD_RES
<222> LOCATION: (6)..(6)
<223> OTHER INFORMATION: Lys or Gln

<400> SEQUENCE: 24

Arg Xaa Gln Lys Xaa Xaa Ala Leu Asn
1               5

<210> SEQ ID NO 25
<211> LENGTH: 52
<212> TYPE: PRT
<213> ORGANISM: Artificial Sequence
<220> FEATURE:
<223> OTHER INFORMATION: Description of Artificial Sequence: Synthetic
      WALLDOF motif consensus sequence

<400> SEQUENCE: 25

Cys Pro Arg Cys Asn Ser Thr Asn Thr Lys Phe Cys Tyr Tyr Asn Asn
1               5                   10                  15

Tyr Ser Leu Thr Gln Pro Arg Tyr Phe Cys Lys Thr Cys Arg Arg Tyr
            20                  25                  30

Trp Thr Asp Gly Gly Ser Leu Arg Asn Ile Pro Val Gly Gly Gly Ser
        35                  40                  45

Arg Lys Asn Lys
    50

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
      WALLDOF motif consensus sequence
<220> FEATURE:
<221> NAME/KEY: MOD_RES
<222> LOCATION: (2)..(2)
<223> OTHER INFORMATION: Glu or Gln
<220> FEATURE:
<221> NAME/KEY: MOD_RES
<222> LOCATION: (4)..(4)
<223> OTHER INFORMATION: Ala, Pro or Gln
<220> FEATURE:
<221> NAME/KEY: MOD_RES
<222> LOCATION: (5)..(5)
<223> OTHER INFORMATION: His, Gln or not present
<220> FEATURE:
<221> NAME/KEY: MOD_RES
<222> LOCATION: (10)..(10)
<223> OTHER INFORMATION: Ala or Ser
<220> FEATURE:
<221> NAME/KEY: MOD_RES
<222> LOCATION: (11)..(11)
<223> OTHER INFORMATION: Phe or Tyr

<400> SEQUENCE: 26

His Xaa Gly Xaa Xaa Asp Leu Asn Leu Xaa Xaa Pro
1               5                   10

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      WALLDOF motif consensus sequence
<220> FEATURE:
<221> NAME/KEY: MOD_RES
<222> LOCATION: (2)..(2)
<223> OTHER INFORMATION: Ala, Pro or Gly
<220> FEATURE:
<221> NAME/KEY: MOD_RES
<222> LOCATION: (3)..(3)
<223> OTHER INFORMATION: Leu or Met

<400> SEQUENCE: 27

Ser Xaa Xaa Glu Leu Leu
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      WALLDOF motif consensus sequence
<220> FEATURE:
<221> NAME/KEY: MOD_RES
<222> LOCATION: (1)..(1)
<223> OTHER INFORMATION: Leu, Phe or Gln
<220> FEATURE:
<221> NAME/KEY: MOD_RES
<222> LOCATION: (2)..(2)
<223> OTHER INFORMATION: Gly or Asn
<220> FEATURE:
<221> NAME/KEY: MOD_RES
<222> LOCATION: (6)..(6)
<223> OTHER INFORMATION: Asp or Glu

<400> SEQUENCE: 28

Xaa Xaa Phe Ser Leu Xaa
1               5

<210> SEQ ID NO 29
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      WALLDOF motif consensus sequence
<220> FEATURE:
<221> NAME/KEY: MOD_RES
<222> LOCATION: (2)..(2)
<223> OTHER INFORMATION: Ile, Leu or Met
<220> FEATURE:
<221> NAME/KEY: MOD_RES
<222> LOCATION: (6)..(6)
<223> OTHER INFORMATION: May or may not be present
<220> FEATURE:
<221> NAME/KEY: MOD_RES
<222> LOCATION: (7)..(7)
<223> OTHER INFORMATION: Phe, Ile, Val or Leu
<220> FEATURE:
<221> NAME/KEY: MOD_RES
<222> LOCATION: (12)..(12)
<223> OTHER INFORMATION: Pro or Gln

<400> SEQUENCE: 29

Arg Xaa Leu Phe Pro Thr Xaa Glu Asp Leu Lys Xaa
1               5                   10

<210> SEQ ID NO 30
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe or Tyr

<400> SEQUENCE: 30

Gly Xaa Trp
1
```

US 9,267,146 B2

INCREASING CELL WALL DEPOSITION AND BIOMASS DENSITY IN PLANTS

CROSS-REFERENCE TO RELATED PATENT APPLICATIONS

This application is the U.S. National Phase of PCT/IB32009/006603 filed Aug. 21, 2009 which claims priority from U.S. provisional application Ser. No. 61/091,075, filed Aug. 22, 2008, the contents of each are incorporated herein by reference in entirety.

SEQUENCE LISTING

The instant application contains a Sequence Listing which has been submitted in ASCII format via EFS-Web and is hereby incorporated by reference in its entirety. Said ASCII copy, created on Aug. 16, 2013, is named 034559.00060_SL.txt and is 46,406 bytes in size.

FIELD OF THE INVENTION

The present invention relates to crops with enhanced efficiency of packaging fixed carbon into storage compounds. More particularly, methodology and constructs are directed to increasing cell wall deposition and/or biomass of plants.

BACKGROUND OF THE INVENTION

Perennial crops such as sugarcane, switchgrass, *Miscanthus* and woody species are major sources of carbon fixed in the form of simple sugars or complexes mixtures of cellulose and hemicellulose. These biomass resources are major targets for the several industries, such as the bioenergy industry, that are currently focused on developing resources demanded by the increasing world population.

Biomass resources are useful, for example, for the production of cellulosic ethanol that could potentially displace 30% of USA current petroleum consumption in the near future. Perlack et al., BIOMASS AS FEEDSTOCKS FOR A BIOENERGY AND BIO-PRODUCTS INDUSTRY: THE TECHNICAL FEASIBILITY OF A BILLION-TON ANNUAL SUPPLY, ORNL/TM-2005/66 (2005). These lignocellulosic feedstocks have been proposed to offer environmental and economic advantages over current energy resources, because they require fewer agricultural inputs than annual crops and can be grown on agriculturally marginal lands. Hill et al., *Proc. Natl. Acad. Sci. USA,* 103: 11206-210 (2006).

Projections have been made showing that the world demand for wood is expected to grow by 20% in the next decade, due to an increasing usage of forest products, woody residues, and woody energy crops for electricity, fuel and biomaterial production. Strauss and Bradshaw, TREE BIOTECHNOLOGY IN THE NEW MILLENNIUM: INTERNATIONAL SYMPOSIUM ON ECOLOGICAL AND SOCIETAL ASPECT OF TRANSGENIC PLANTATIONS, Oregon State University (2001); Mead, *Biomass and Bioenergy,* 28: 249-66 (2005).

Therefore there is a need to develop highly productive tree plantations to reduce the pressure on natural forests, preceded by extensive breeding advances in plantation tree species such as poplar and *eucalyptus*. Until now this has been difficult because the long generation time in trees makes conventional breeding a very slow process. Genetic engineering techniques have the potential to greatly shorten the breeding timeline for trees and allow for more targeted breeding.

Approaches to increase carbon allocation to the above ground portions of plants would increase growth rates and biomass yields. Ragauskas et al., *Science,* 311: 484-89 (2006). In trees the fixed carbon is accumulated mainly in the secondary walls of the cells, which are the major constituent of wood. Secondary walls are composed mainly of cellulose, hemicelluloses and lignin. During secondary wall formation, the biosynthesis of these cell wall components is highly coordinated and depends of master regulatory genes controlling a huge array of individual genes. Despite the advances in the study of secondary wall biosynthetic genes, little is known about the molecular mechanisms underlying the coordinated expression of these genes during wood formation. Zhong et al., *Plant Cell,* 19: 2776-92 (2006).

There are several types of regulatory processes controlling gene expression, protein production, and protein processing and protein activity. One of such processes involves the activity of transcription factors, which are proteins capable of recognizing sequences in the promoter of genes and, by binding in such particular sequences, modulate the transcription rate of such genes. Several transcription factors have been identified in a number of organisms and their role in controlling particular biosynthetic pathways has been established. For example, transcriptional profiling of genes differentially expressed during in vitro xylem differentiation in *Zinnia* (Demura et al., *Proc. Natl. Acad. Sci. USA,* 99: 15794-99, 2002) and *Arabidopsis* (Kubo et al., *Genes Dev.,* 19: 1855-60, 2005) or during secondary growth in *Arabidopsis* stems and roots (Oh et al., *J. Exp. Bot.,* 54: 2709-22, 2003; Zhao et al., *Plant Physiol.,* 138: 803-18, 2005) and poplar (Hertzberg et al., *Proc. Natl. Acad. Sci. USA,* 98: 14732-137, 2001) has led to the identification of diverse families of transcription factors, which may be involved in the regulation of xylem differentiation or secondary growth. Similarly, microarray analysis showed that 182 transcription factors are differentially expressed during different developmental stages of *Arabidopsis* inflorescence stems. Ehlting et al., *Plant J.,* 42: 618-40 (2005). Although the exact functions of most of these xylem- or secondary growth-associated transcription factors are unknown, they provide useful tools to dissect the molecular mechanisms controlling the complex process of xylem development, including the initiation of differentiation, cell elongation and secondary wall thickening.

Among these xylem- or secondary growth-associated transcription factors are a group of DOF (for DNA-binding with One Finger) domain transcription factors. DOF proteins are plant-specific transcription factors that share a highly conserved N-terminal DNA-binding domain and a C-terminal domain for transcriptional regulation. Yanagisawa, *Trends Plant Sci.,* 7: 555-60 (2002). The DNA-binding domain is characterized by 52 amino acid residues structured as a Cys2/Cys2 $Zn^{2+}$ finger, which recognizes cis-regulatory elements containing the common core 5'-AAAG-3' (SEQ ID NO: 5). Umemura et al., *Plant J.,* 37: 741-49 (2004); Yanagisawa & Schmidt, *Plant J.,* 17: 209-14 (1999).

DOF proteins have been suggested to participate in the regulation of biological processes exclusive to plants such as light-regulated gene expression, photosynthetic carbon assimilation, accumulation of seed-storage proteins, germination, response to phytohormones, guard cell-specific gene expression, flavonoid metabolism and lipid biosynthesis. Plesch et al., *Plant J.,* 28: 455-64 (2001); Moreno-Risueno et al., *Plant J.,* 51: 352-65 (2007); Wang et al., *Plant J.,* 52: 716-29 (2007).

In rice the most presented cis element for all seed-preferential transcriptional factor genes was found to be 'AAAG' (SEQ ID NO: 5), the core site required for binding of D of proteins, suggesting an essential and most remarkable role of DOF transcription factors in hierarchical regulatory networks controlling rice seed development. Duan et al., *Plant Mol. Biol.*, 57: 785-804 (2005).

Maize DOF1 expresses in leaves, stems and roots and has different transactivation activities in greening and etiolated protoplasts. DOF1 is activated in illuminated leaf cells and may be involved in the light regulation of genes coupled to light-dependent processes. Yanagisawa and Sheen, *Plant Cell*, 10: 75-90 (1998). Maize DOF1 also has been suggested to be a regulator for C4 photosynthetic phosphoenolpyruvate carboxylase, which catalyzes the primary fixation of $CO_2$ in the C4 photosynthetic pathway. Additionally, it enhances transcription from the promoter of a cytosolic orthophosphate dikinase. Both enzymes are involved in amino acid synthesis and the recapture of respired $CO_2$. It has been proposed that maize DOF1 might play a more general role in the expression of multiple genes related to carbon metabolism. See Yanagisawa, *Plant J.*, 21: 281-88 (2000).

Another maize endosperm-specific DOF protein, named prolamin-box binding factor (PBF), was shown to interact with the basic leucine zipper protein Opaque2, a known transcriptional activator of prolamin gene expression (Vicente-Carbajosa et al., *Proc. Natl. Acad. Sci. USA*, 94: 7685-90, 1997). Other homologous proteins exist in the endosperm of other cereals, such as BPBF (barley PBF) and WPBF (wheat PBF), both with similar DNA-binding properties as maize PBF. These observations suggest an evolutionary conservation of the PBF gene function, as an important regulator of storage protein gene expression among small grain cereals, and support a scenario where protein-protein interactions are important in the DOF functions. Mena et al., *Plant J.*, 16: 53-62 (1998).

In rice there is a member of the DOF family (OSDOF3) that has been shown to interact with a R2R3-type MYB transcription factor in the aleurone layer, resulting in the induced expression of a number of genes encoding hydrolytic enzymes (α-amylases and β-glucanases) that participate in the mobilization of stored molecules. Washio, *Plant Physiol.*, 133: 850-63 (2003). Gene regulation in these aleurone cells is under the control of phytohormones, mainly the ratio of gibberellins (GA) to abscisic acid (ABA). The observed accumulation pattern of the barley PBF transcript upon seed imbibition suggested that it may be up-regulated by GA and function as a transcriptional repressor upon germination through interaction with the pyrimidine box of the GARC (GA responsive complex), a conserved cis-element required for GA induction identified in hydrolase genes from cereals. Mena et al., *Plant Physiol.*, 130: 111-19 (2002).

In *Arabidopsis* there are 36 members of the DOF family, two of which, DAG1 and DAG2 (Dof Affecting Germination), also affect seed germination by light response and gibberellin concentration, possibly playing opposite regulatory roles on the same maternal gene(s). Gualberti et al., *Plant Cell*, 14: 1253-63 (2002).

Additionally, DOF proteins have been described as part of a regulatory network controlling secondary metabolites. In this regard, OBP2, a DOF gene prominently expressed in the phloem of leaves and other organs in *Arabidopsis*, has been shown to activate expression of CYP83B1, a gene that participates on the synthesis of glucosinolates, a group of secondary metabolites that function as defense substances against herbivores and micro-organisms. Skirycz et al., *Plant J.*, 47: 10-24 (2006). Another *Arabidopsis* DOF gene member, AtDOF4;2, was identified as a gene inducing a bushy plant phenotype and potentially being involved in the regulation of phenylpropanoid metabolism.

Constitutive overexpression and RNAi-mediated silencing of AtDOF4;2 caused reciprocal changes in the expression of flavonoid biosynthetic genes and the accumulation of flavonoids under cold and high-light conditions. See Skirycz et al., *New Phytol.*, 175: 425-38 (2007).

The participation of DOF proteins in the regulation of phenylpropanoid metabolism has also been shown in *Arabidopsis thaliana* mutants de-etiolated3 (det3), pom-pom1 (pom1) and ectopic lignification1 (eli1). These mutants deposit lignins in cells where these polymers would not normally be found. Microarray analysis suggests that changes in the expression of specific members of the R2R3-MYB and DOF transcription factor families may contribute to the ectopic lignifications phenotypes in these mutants. Rogers et al., *New Phytol.*, 168: 123-40 (2005).

In poplar there are 41 DOF genes, according to Yang et al., *Plant Physiol.*, 142: 820-30 (2006). A sequence analysis of these genes along with 36 *Arabadopsis* and 30 rice DOF genes revealed 41 conserved motifs, of which one:

```
                                            (SEQ ID NO: 6)
EILKCPRCDSMNTKFCYYNNYNLSQPRHFCKTCRRYWTKGGALRNVP
VGGGCRKNKR,
``` was identified as the DOF domain. Id., page 824 and Table I. A maximum-likelihood phylogenetic tree, constructed using full-length protein sequences of these DOF genes, also highlighted 27 pairs of paralogous genes in the terminal nodes of the tree. Id., page 825 and FIG. 2.

SUMMARY OF THE INVENTION

Based on the inventors' discoveries and related insights about DOF proteins, provided in this description is, among other things, a methodology for increasing cell wall deposition and/or biomass. The inventive method comprises modulating expression of a walldof sequence in a plant cell, e.g., by effecting overexpression of such sequence in a transgenic plant, such that the plant is characterized by an increased biomass density. In a preferred embodiment, the transgenic plant is the product of a process comprising: (a) providing regenerable plant material that is transformed with a construct comprised of a walldof DNA sequence and, operably linked thereto, a promoter that is active in plant cells; and then (b) subjecting the material or plants regenerated from the material to a selection for which at least one selection criterion is increased cell wall deposition or increased biomass density, relative to a non-transformed state. Illustrative of the walldof DNA sequence are (i) the nucleotide sequence set out in SEQ ID NO: 1 and (ii) the nucleotide sequence that encodes the amino acid sequence set out in SEQ ID NO: 2.

Also contemplated is a construct comprised of a walldof DNA sequence and, operably linked thereto, a promoter that is active in plant cells. In both the construct and the above-mentioned method, the promoter can be, for example, a tissue- or organ-specific promoter, such as a xylem-specific promoter; a tissue- or organ-preferred promoter, such as a xylem-preferred promoter, a constitutive promoter, or an inducible promoter.

By the same token, related aspects include a transgenic plant cell that comprises a heterologous walldof DNA sequence that is expressed under the control, for instance, of a tissue- or organ-specific/preferred promoter, constitutive promoter, or inducible promoter. Also provided is a transgenic plant that expresses a walldof DNA sequence such that the plant is characterized by increased biomass density, relative to a non-transformed state.

BRIEF DESCRIPTION OF THE DRAWINGS

FIG. 3 shows multiple alignments of dicotyledons WALLDOFs in which conserved motifs 1 to 7 are highlighted. (SEQ ID NOS: 11, 12, 13, 14, 2, 15, 16, and 17, in order of appearance)

FIG. 4 shows multiple alignments of monocotyledons WALLDOFs (in which conserved motifs 1 to 7 are highlighted.) (SEQ ID NOS: 18-23, in order of appearance)

DETAILED DESCRIPTION OF THE INVENTION

The present inventors demonstrated that a poplar DOF transcription factor, called WALLDOF, plays an essential role in secondary cell wall deposition. Thus, in planta overexpression of a walldof gene under the control, e.g., of a poplar xylem-specific promoter, results in plants that display a dramatic increase in secondary wall deposition and increased biomass.

Although the inventors are not bound to any particular theory, WALLDOF is understood to function as a transcriptional switch for the developmental program of secondary wall deposition. Accordingly, the present invention relates to methodology and to DNA constructs for modulating the level of WALLDOF or another, related transcription factor in a plant, the genetic constituency of which reflects an introduction, preferably infra-genomic, of a DNA segment encoding such a transcription factor, thereby to increase cell wall deposition and/or biomass density of the plant.

In this regard, the term "expression" denotes the production of a product that is or that is related to a protein encoded by the nucleotide sequence of a DNA segment ("gene product"). "Overexpression" refers to production in a transgenic organism of a gene product at a level exceeding the production level for that product in a normal (non-transgenic) organism. In this sense, "overexpression" does not require endogenous expression of the gene product in the non-transgenic organism. For example, overexpression could occur by de-repression of a gene or repression of an inhibitory factor.

Therefore, one may speak of overexpression as a means for "modulating" expression of a DNA that codes for WALLDOF or a related transcription factor (see further discussion below). As a function of context, "modulating" or "modulate" also may have a connotation drawn from common usage in the molecular biology of regulatory proteins; that is, the binding by a regulatory protein of promoters for genes that are related functionally to a biological process, such as cell wall deposition, is said to "modulate" those genes by increasing or decreasing their respective expression levels. Accordingly, in planta overexpression of WALLDOF, would be expected to modulate key genes controlling cell wall deposition and biomass density, such that their expression levels would be increased or decreased.

Figure 5:
FIG. 5 shows in (A) the order and size WALLDOF motifs and in (B) the amino acid consensus sequence of WALLDOF motifs 1 to 7. (SEQ ID NOS: 24-30, in order of appearance)

For present purposes, the class of suitable transcription factors accommodates substitutions, additions, and deletions in relation to SEQ ID NO: 2 that do not alter the regulatory function that characterizes the class. Illustrative of such changes are those shown in present FIG. 5B, discussed below.

By the same token, there is comprehended a class of DNAs, coding for such transcription factor, that can be identified and functionally annotated by sequence comparison, pursuant to any of a number of algorithms available for grouping gene sequences on the basis of clustering or alignment criteria, as illustrated by Yang et al. (2006), infra. Thus, the present disclosure encompasses orthologs and paralogs of a gene comprised of the nucleotide sequence set forth in SEQ ID NO: 1, as well as other DNAs that code for a protein sequence that is functionally related, as described above, to the amino acid sequence set forth in SEQ ID NO: 2.

An individual knowledgeable in plant molecular biology also can identify such DNAs via conventional methodology involving the screening of cDNA libraries or genomic libraries with suitable hybridization probes. In particular, paralog and ortholog sequences can be isolated with the aid of (degenerate) oligonucleotides and PCR-based methods exemplified, for instance, by PCR—THE BASICS 2$^{nd}$ ed. (Taylor & Francis, 2006); PCR PROTOCOLS—METHODS IN MOLECULAR BIOLOGY 2$^{nd}$ ed. (Humana Press, 2003); REAL TIME PCR (BIOS ADVANCED METHODS) 1$^{st}$ ed. (Taylor & Francis, 2006).

Accordingly, the phrase "walldof DNA sequence" denotes a nucleic acid molecule with a nucleotide sequence that hybridizes under stringent conditions with the sequence set forth in SEQ ID NO: 1 and that codes for a transcription factor that belongs to the functional class, described above, inclusive of any protein comprising the amino acid sequences set forth in SEQ ID NO: 2. (Italicization in this description denotes a gene, and capitalization an encoded product.) The category of walldof DNA sequences also includes sequences with at least 40%, preferably at least 60%, especially preferably at least 80% and particularly preferably at least 90%, 91%, 92%, 93%, 94%, 95%, 96%, 97%, 98%, or 99% identity with the nucleotide sequence shown in SEQ ID NO: 1. The determination of percentage identity in this regard is discussed in greater detail below.

In one embodiment, an inventive construct comprises a walldof DNA sequence operably linked to a tissue-preferred promoter, which can be but is not limited to a vascular-preferred promoter, a xylem-preferred promoter, a cambium-preferred promoter, a stem-preferred promoter, a wood-preferred promoter, a stalk-preferred promoter, and a parenchyma cell-preferred promoter. Illustrative of suitable promoters in this regard is the set of xylem-preferred promoter disclosed in published PCT application WO 2005/096805, which is incorporated here by reference. Alternatively, the DNA construct of the invention comprises a walldof DNA sequence operably linked to a constitutive promoter, an inducible promoter, a tissue- or organ-specific promoter, a tissue- or organ-preferred promoter, or any other suitable promoter.

Accordingly, suitably regenerable plant material, such as callus, is transformed with a DNA construct as described above, and from the transformed plant material a plant is obtained in conventional fashion, as a primary transformant or progeny thereof, in which plant the level of the transcription factor is increased. As a consequence, the plant displays an increase in cell wall deposition and in biomass density, relative to a plant in which the level of transcription factor is not increased by the genetic engineering methodology disclosed herein.

Figure 6:
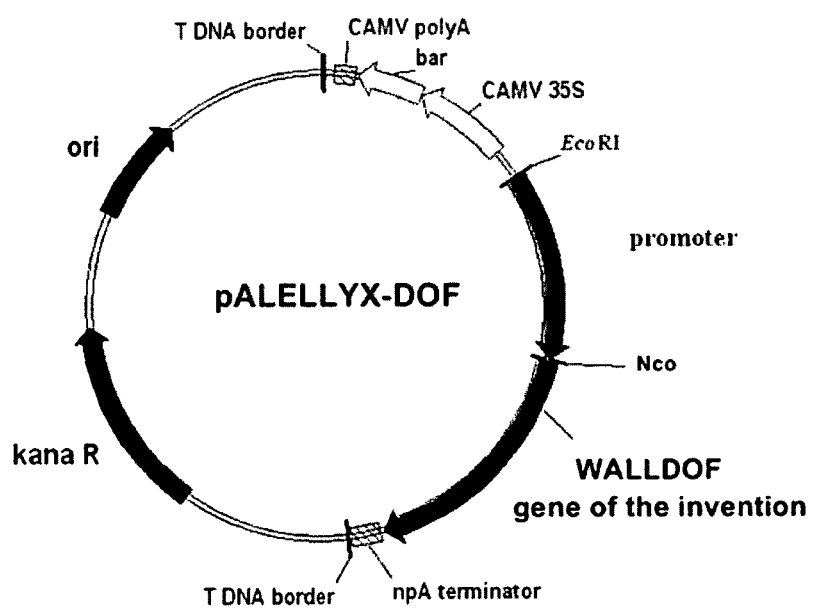
FIG. 6 schematically illustrates the plant expression plasmidial vector pALELLYX-DOF of the invention comprising a cambium/xylem preferred promoter driving the expression of a *Populus deltoides* DOF (walldof) nucleotide sequence of the invention.

As discussed above, therefore, in one embodiment it is desirous to provide a plant transformed with a DNA construct depicted, for illustrative purpose, in the FIG. 6. For instance, a transformed plant of the invention, having incorporated in its genome the DNA construct described above, expresses a polypeptide comprising the amino acid sequence set forth in SEQ ID NO: 2 at high levels, resulting in increased cell wall deposition and/or increased biomass density, relative to a non-transformed state (i.e., when compared with a non-transformed plant of the same type or variety).

In accordance with other embodiments, modulating expression of a walldof DNA sequence in a plant causes an increase in the wall area per cell and the percentage of the wall area over the total cell area. Because wall area per cell and the percentage of the wall area over the total cell area are positively correlated with biomass density, such modulation results in increased biomass density.

Pursuant to certain aspects, modulating the expression of a walldof DNA sequence in a plant cell, such as an angiosperm plant cell or gymnosperm xylary tracheid, increases the cell wall deposition, as visualized and measured by standard histochemical, chemical and physical analyses. For example, see A GUIDE TO WOOD MICROTOMY: MAKING QUALITY MICROSLIDES OF WOOD SECTIONS, 1$^{st}$ ed., Ives, ed. Ives, Suffolk, 2001; PLANT MICROTECHNIQUE AND MICROSCOPY, Ruzin, ed. Oxford University Press, New York, 1999; CHARACTERIZATION OF LIGNOCELLULOSIC MATERIALS, Hu, ed. Blackwell Publishing, 2008; PREPARATION OF WOOD FOR CHEMICAL ANALYSIS, Tappi T 264 cm-97, Tappi Press, Atlanta, 1997.

More generally, methodology and constructs described herein can be implemented to increase biomass density in a wide range of plants, such as but not limited to *Eucalyptus* ssp, *Poplar* ssp, conifers, willow, sugarcane, sorghum, wheat, corn, cotton, soybean, alfalfa, vegetables (including but not limited to broccoli, cauliflower, cabbage, radish, Chinese cabbage, onion, carrot, cucumber, pepper, tomato, eggplant, squash, gourds, pumpkin, okra, spinach, dry bean, pea, leek, lettuce, fennel, garden bean, sugar beets, etc.), melons, watermelons, canola (rapeseed), rice, barley, peanut, pigeon pea, millet, grape, berries (including but not limited to blue, black, raspberry, mulberry, cranberry, boisen berry, etc.), fruits from trees (including but not limited to plum, peach, nectarine, apricot, kiwi, pomegranate, mango, fig, orange, lemon, lime, blood orange, grapefruit, apple, banana, and the like), nut trees (cocounut, walnut (English and black), pecan, almond, hazelnut, Brazil nut, hickory nut, acorn), oilseed producing plants (including but not limited to sunflower, rapeseed, etc.) sudan grass, miscanthus, switchgrass, elephant grass, and fountain grass, among others.

Using the methodologies and constructs disclosed herein, a plant can be genetically engineered to increase biomass for a variety of applications and industries, including but not limited to pulp and paper industry, general forestry, biomass feedstock, biomaterials for bioenergy, cereals, beverages, confectionaries, sugars and sweeteners; fibers; dyes; tannins; paints; resins; latexes, hydrogels, paints, oils, waxes, perfumes, floral and ornamentals, food colorings, spices, herbs, medicinals, pharmaceuticals, nutraceuticals, bamboo, cork, and wood.

Thus, depending on the plant and the particular biomass needed for a given application or industry, a plant with increased biomass or biomass density may exhibit one or more of the following non-limiting phenotypes, increased height; weight, size or numbers of leaves; length and thickness of shoots; length, thickness and branching of roots; seed production per plant; flowering; numbers and sizes of cells in tissues, including wood-forming tissues; and development of plant reproductive organs.

All technical terms in this description are in common use in biochemistry, molecular biology or agriculture and have their conventional meaning, unless indicated otherwise indicated. Such meaning is memorialized, for example, in: MOLECULAR CLONING: A LABORATORY MANUAL, 3rd ed., vol. 1-3, ed. Sambrook and Russel, Cold Spring Harbor Laboratory Press, Cold Spring Harbor, N.Y., 2001; CURRENT PROTOCOLS IN MOLECULAR BIOLOGY, ed. Ausubel et al., Greene Publishing Associates and Wiley-Interscience, New York, 1988 (with periodic updates); SHORT PROTOCOLS IN MOLECULAR BIOLOGY: A COMPENDIUM OF METHODS FROM CURRENT PROTOCOLS IN MOLECULAR BIOLOGY, 5$^{th}$ ed., vol. 1-2, ed. Ausubel et al., John Wiley & Sons, Inc., 2002; GENOME ANALYSIS: A LABORATORY MANUAL, vol. 1-2, ed. Green et al., Cold Spring Harbor Laboratory Press, Cold Spring Harbor, N.Y., 1997.

Methodologies involving plant biology techniques are described here and also are described in detail in treatises such as METHODS IN PLANT MOLECULAR BIOLOGY: A LABORATORY COURSE MANUAL, ed. Maliga et al., Cold Spring Harbor Laboratory Press, Cold Spring Harbor, N.Y., 1995. Various techniques using PCR are described, e.g., in Innis et al., PCR PROTOCOLS: A GUIDE TO METHODS AND APPLICATIONS, Academic Press, San Diego, 1990 and in Dieffenbach and Dveksler, PCR PRIMER: A LABORATORY MANUAL, 2$^{nd}$ ed., Cold Spring Harbor Laboratory Press, Cold Spring Harbor, N.Y., 2003. PCR-primer pairs can be derived from known sequences by known techniques such as using computer programs intended for that purpose, e.g., Primer, Version 0.5, 1991, Whitehead Institute for Biomedical Research, Cambridge, Mass. Methods for chemical synthesis of nucleic acids are discussed, for example, in Beaucage and Caruthers, *Tetra. Letts.* 22: 1859-62 (1981), and Matteucci and Caruthers, *J. Am. Chem. Soc.* 103: 3185 (1981).

Restriction enzyme digestions, phosphorylations, ligations and transformations were done as described in Sambrook et al., MOLECULAR CLONING: A LABORATORY MANUAL, $2^{nd}$ ed. (1989), Cold Spring Harbor Laboratory Press. Unless otherwise specified, all reagents and materials used for the growth and maintenance of bacterial cells were obtained from Aldrich Chemicals (Milwaukee, Wis.), DIFCO Laboratories (Detroit, Mich.), Invitrogen (Gaithersburg, Md.), or Sigma Chemical Company (St. Louis, Mo.).

The terms "encoding" and "coding" refer to the process by which a gene, through the mechanisms of transcription and translation, provides information to a cell from which a series of amino acids can be assembled into a specific amino acid sequence to produce an active protein. Because of the degeneracy of the genetic code, certain base changes in DNA sequence do not change the amino acid sequence of a protein. Accordingly, the present disclosure encompasses any modification to a nucleotide sequence that does not substantially affect the functional properties of an encoded protein.

The term "alignment" refers here to a number of nucleotide or amino acid sequences aligned by lengthwise comparison so that components, i.e., nucleotide bases or amino acids residues, in common ("identical"), "similar" and/or different may be readily and graphically identified. Additionally, the term "alignment" includes global and local alignments between any two or more sequences. Among other applications, "alignment" may be used to determine the numbers of components in common ("identical") and therefore the "identity" between two or more nucleotide or peptide sequences. "Alignment" may also be used to determine the numbers of "similar" components and therefore "similarity" between two or more nucleotide or peptide sequences. Thus, "alignment" may be used to determine "homology" between sequences and to identify "conserved domains" and relatedness within these domains. Sequence alignments and scores for percentage sequence identity and/or similarity may be determined using computer programs known in the art, such as GCG Wisconsin version 10.3 Package, available from Accelrys Inc., 9685 Scranton Road, San Diego, Calif. 92121-3752 USA, or EmbossWin version 2.10.0 (using the program "needle"). Alternatively, percent similarity or identity may be determined by searching against databases, using algorithms such as FASTA, BLAST, among any others.

The terms "identity" and "similarity," as well as "identical" and "similar," respectively, can be determined by alignment of at least two peptide or two nucleotide sequences, via a global and/or a local alignment algorithm. Identity values are the numbers or percent values of positions that, after alignment with at least one of the sequences provided herein, have exactly the same nucleotides or amino acids at the same positions in a given sequence. Similarity values are the numbers or percent values of positions that, after alignment with at least one of the sequences provided herein, have similar nucleotides or amino acids at the same positions in a given sequence. It is therefore understood that similar amino acids are those with similar properties, which includes but is not limited to acidic amino acids, basic amino acids, aromatic amino acids, aliphatic amino acids, polar amino acids and non-polar amino acids, among other properties. It is also therefore understood that "identical" nucleotides or amino acids are considered "similar," too. Thus, sequences may be referred to as "substantially identical" or "essentially similar" when they share at least 90% and 70% of sequence identity over their entire length, respectively.

The term "homology," as used in this description, refers to sequence similarity between a reference sequence provided herein and at least a fragment of a newly sequenced clone insert or its encoded amino acid sequence. Sequences that are homologous, i.e., that share significant sequence similarity, to any sequence(s) disclosed herein are also contemplated. In addition, sequences that are homologous to those disclosed herein can be derived from any plant of choice, including monocots and dicots, and particularly agriculturally important plant species. Several different methods are known for identifying and defining these functionally homologous sequences, which could be classified as "orthologs" and "paralogs," respectively. Orthologs are genes, in different species, that have a similar sequence and similar function(s) and that are derived via a speciation event. Because plants have common ancestors, many genes in any plant species will have a corresponding orthologous gene in another plant species. Once an orthologous sequence has been identified, the function of the "ortholog" can be deduced from the identified function of the reference sequence. Paralogs are structurally related genes within a single species and are derived by a duplication event, whereby the respective encoded proteins may retain similar functions. For present purposes, a suitable paralog of a gene comprised of the nucleotide sequence set forth in SEQ ID NO: 1 should code for a protein with comparable transcriptional regulatory activity.

By the phrase "isolated nucleic acid molecule(s)" is intended a nucleic acid molecule, DNA or RNA, that has been removed from its native environment. For example, recombinant DNA molecules contained in a DNA construct are considered isolated for the purposes of the present invention. Further examples of isolated DNA molecules include recombinant DNA molecules maintained in heterologous host cells or DNA molecules that are purified, partially or substantially, in solution. Isolated RNA molecules include in vitro RNA transcripts of the DNA molecules of the present invention. Isolated nucleic acid molecules further include such molecules produced synthetically.

The phrase "heterologous nucleic acid" refers to a nucleic acid, DNA or RNA, which has been introduced into a cell (or the cell's ancestor). Such heterologous nucleic acid may comprise segments that are a copy of a sequence which is naturally found in the cell into which it has been introduced, or fragments thereof.

The present disclosure provides methodology and constructs for increasing cell wall deposition and plant biomass density. As a non-limiting example, increasing cell wall deposition and wood density in poplar is provided. Wood is essentially a matrix of cell walls and cellular air spaces from secondary xylem. Megraw, WOOD QUALITY FACTORS IN LOBLOLLY PINE (Tappi Press, 1985), page 88. In this sense, wood density is determined by the cell wall thickness, the cross-sectional area of the lumen of the vessels, and the number of the vessels involved in water transport through the stem. Roderick and Berry, *New Phytol.* 149: 473 (2001); Preston et al., *New Phytologist* 170: 807-18 (2006). It has been shown in *Eucalyptus* and other angiosperm species that wood density negatively correlates with hydraulic conductivity and the cross-sectional area of the vessels. Thomasa et al., *Forest Ecology and Management* 193: 157-65 (2004); Preston et al., *New Phytologist,* 170: 807-18 (2006). Other non-limiting examples include increasing cell wall deposition and/or biomass in a variety of plants, such as soybean, corn, wheat, canola, cotton, soy, canola, alfalfa, sugarcane, and rice, for a variety of applications including but not limited to cereals; beverages; confectionaries; sugars and sweeteners; animal feed; fibers; dyes; tannins; paints; resins; latexes; hydrogels; paints; oils; waxes; perfumes; florals and ornamentals; food colorings; spices; herbs; medicinals; pharmaceuticals; and nutraceuticals.

Nucleotide and Polypeptide Sequences

Walldof DNA sequences are illustrated by but not limited to the sequence set forth in SEQ ID NO: 1, as well as by nucleic acid molecules comprised of variants of SEQ ID NO: 1, with one or more bases deleted, substituted, inserted, or added, which variants code for polypeptides characterized by WALLDOF activity, as described above.

A "variant" is a nucleotide or amino acid sequence that deviates from the standard, or given, nucleotide or amino acid sequence of a particular gene or protein. The terms "isoform," "isotype," and "analog" also refer to "variant" forms of a nucleotide or an amino acid sequence. An amino acid sequence that is altered by the addition, removal, or substitution of one or more amino acids, or a change in nucleotide sequence may be considered a "variant" sequence. The variant may have "conservative" changes, wherein a substituted amino acid has similar structural or chemical properties, e.g., replacement of leucine with isoleucine. A variant may have "nonconservative" changes, e.g., replacement of a glycine with a tryptophan. Analogous minor variations also may include amino acid deletions or insertions, or both. Guidance in determining which amino acid residues may be substituted, inserted, or deleted can be found using well-known computer programs such as Vector NTI Suite (InforMax, Md.). "Variant" also may refer to a "shuffled gene" as described, for example, in several patents assigned to Maxygen, Inc. (Redwood City, Calif.), such as U.S. Pat. No. 6,251,674 and U.S. Pat. No. 6,500,639. Accordingly, a "variant" may be drawn from variants of sequences and desired polynucleotides that are modified according to the methods and rationale disclosed in U.S. Pat. No. 6,132,970, which is incorporated herein by reference.

Exemplary WALLDOF polypeptide sequences include but are not limited to the sequence set forth in SEQ ID NO: 2, as well as polypeptide sequences having one or more amino acids substituted, deleted, inserted, or added yet retaining WALLDOF activity. WALLDOF sequences include polypeptide sequences having at least one amino acid consensus motif, preferably at least two amino acid consensus motifs, more preferably at least three amino acid consensus motifs, more preferably at least four amino acid consensus motifs, more preferably at least five amino acid consensus motifs, most preferably at least six amino acid consensus motifs and most preferably the seven amino acid consensus motifs as described in FIG. 5. The present disclosure also encompasses one or more WALLDOF conserved domains formed by at least one amino acid consensus motif, preferably at least two amino acid consensus motifs, more preferably at least three amino acid consensus motifs, more preferably at least four amino acid consensus motifs, more preferably at least five amino acid consensus motifs, most preferably at least six amino acid consensus motifs and most preferably the seven amino acid consensus motifs as described in FIG. 5.

Additionally, multiple forms of WALLDOF may exist, which may be due to post-translational modification of a gene product, or to multiple forms of the respective walldof genes. Sequences that have such modifications and that code for a WALLDOF transcription factor are also included.

In this description, a "conserved domain" or a "conserved region" is a region that is highly conserved among certain polynucleotide or polypeptide sequences, i.e., where there is a relatively high degree of sequence similarity between the distinct sequences. Also, these terms refers to domains of polypeptide sequences, which are encoded by polynucleotide sequences, that forms three-dimensional structures and functional units relatively conserved along evolution. The phrases "conserved domain" or "conserved region" also encompass compact, local, and semi-independent units, often stable and independently folded, formed by packing of "amino acid consensus motifs" coded by polynucleotide sequences.

The phrase "amino acid consensus motif" refers to the portion or subsequence of a polypeptide sequence that is substantially conserved among polypeptides.

Sequence Analysis

Included in the category of "variant" sequences are sequences that hybridize to a reference walldof DNA sequence. For present purposes, two sequences hybridize when they form a double-stranded complex in a hybridization solution of 6×SSC, 0.5% SDS, 5×Denhardt's solution and 100 μg of non-specific carrier DNA. See Ausubel et al., supra, at section 2.9, supplement 27 (1994). Sequences may hybridize at "moderate stringency," which is defined as a temperature of 60° C. in a hybridization solution of 6×SSC, 0.5% SDS, 5×Denhardt's solution and 100 μg of non-specific carrier DNA. For "high stringency" hybridization, the temperature is increased to 68° C. Following the moderate stringency hybridization reaction, the nucleotides are washed in a solution of 2×SSC plus 0.05% SDS for five times at room temperature, with subsequent washes with 0.1×SSC plus 0.1% SDS at 60° C. for 1 hour. For high stringency, the wash temperature is increased to 68° C. One with ordinary skill in the art can readily select such conditions by varying the temperature during the hybridization reaction and washing process, the salt concentration during the hybridization reaction and washing process, and so forth. For present purposes, hybridized nucleotides are those that are detected using 1 ng of a radiolabeled probe having a specific radioactivity of 10,000 cpm/ng, where the hybridized nucleotides are clearly visible following exposure to X-ray film at −70° C. for no more than 72 hours.

The present disclosure embraces such nucleic acid molecules that are at least 40%, 45%, 50%, 55%, 60%, 65%, 70%, 75%, 80%, 85%, 90%, 95%, 96%, 97%, 98%, 99% or 100% identical to a nucleic acid sequence described in SEQ ID NO: 1. Preferred are nucleic acid molecules which are at least 95%, 96%, 97%, 98%, 99% or 106% identical to the nucleic acid sequence shown in SEQ ID NO: 1. Differences between two nucleic acid sequences may occur at the 5' or 3' terminal positions of the reference nucleotide sequence or anywhere between those terminal positions, interspersed either individually among nucleotides in the reference sequence or in one or more contiguous groups within the reference sequence.

As a practical matter, stating whether any particular nucleic acid molecule is at least 95%, 96%, 97%, 98% or 99% identical to a reference nucleotide sequence implicates a comparison made between two molecules, using algorithms known in the art and can be determined conventionally using publicly available computer programs such as the BLASTN algorithm. See Altschul et al., *Nucleic Acids Res.* 25: 3389-402 (1997).

Nucleic Acid Constructs

In one aspect, the sequence set forth in SEQ ID NO: 1 is incorporated into a nucleic acid construct that is suitable for introduction into a plant or a cell. Thus, such a nucleic acid construct can be used to modulate walldof gene expression in a plant or plant cell. Modulating walldof gene expression in a plant or plant cell is achieved by incorporating in the nucleic acid construct a promoter such as the ones described in PCT application WO 2005/096805, incorporated above, which effect a tissue-preferred expression. Other tissue-preferred or constitutive promoters can be integrated into a DNA construct.

The cell wall deposition and the plant biomass density may be modified by introducing a nucleic acid construct as described herein. Also provided are plant cells containing such constructs; plants derived there from having modified walldof gene expression and progeny of such plants.

As a source of the nucleic acid sequence encoding WALLDOF, a suitable cDNA or genomic DNA or synthetic polynucleotide may be used. Methods for the isolation of suitable walldof DNA sequences are described, supra. Sequences coding for the whole, or substantially the whole, of the transcription factor thus may be obtained. Suitable lengths of this DNA sequence may be cut out for use by means of restriction enzymes. When using genomic DNA as the source of a partial base sequence for transcription, it is possible to use either intron or exon regions or a combination of both.

To obtain constructs suitable for modifying expression of walldof gene in plant cells, the cDNA sequence as found in the transcription factor cDNA or the gene sequence as found in the chromosome of the plant may be used. Recombinant nucleic acid constructs may be made using standard techniques. For example, the nucleic acid sequence for transcription may be obtained by treating a vector containing said sequence with restriction enzymes to cut out the appropriate segment. The nucleic acid sequence for transcription may also be generated by annealing and ligating synthetic oligonucleotides or by using synthetic oligonucleotides in a polymerase chain reaction (PCR) to give suitable restriction sites at each end. The nucleic acid sequence then is cloned into a vector containing suitable regulatory elements, such as upstream promoter and downstream terminator sequences.

An important aspect of the present disclosure is the use of nucleic acid constructs wherein a WALLDOF-encoding sequence is operably linked to one or more regulatory sequences, which drive expression of the WALLDOF-encoding sequence in certain cell types, organs, or tissues without unduly affecting normal development or plant physiology.

"Promoter" connotes a region of DNA upstream from the start of transcription that is involved in recognition and binding of RNA polymerase and other proteins to initiate transcription. A "constitutive promoter" is one that is active throughout the life of the plant and under most environmental conditions. Tissue-specific, tissue-preferred, organ-specific, organ-preferred, cell type-specific, and inducible promoters constitute the class of "non-constitutive promoters." "Operably linked" refers to a functional linkage between a promoter and a second sequence, where the promoter sequence initiates and mediates transcription of the DNA sequence corresponding to the second sequence. In general, "operably linked" means that the nucleic acid sequences being linked are contiguous.

Promoters useful for expression of a nucleic acid sequence introduced into a cell to increase expression of walldof gene may be constitutive promoters, such as the cauliflower mosaic virus (CaMV) 35S promoter, or tissue-specific, tissue-preferred, organ-specific, organ-preferred, cell type-specific, inducible promoters, or any other suitable promoter(s). For example, by using vascular system-specific, xylem-specific, or xylem-preferred promoters, one can modify WALLDOF activity specifically in many tissues such as vascular tissues, especially xylem. The use of a constitutive promoter in general affects enzyme levels and functions in all parts of the plant, while use of a tissue-preferred promoter permits targeting of the modified gene expression to specific plant parts, leading to a more controllable phenotypes.

Thus, it may be found convenient to use a promoter that drives expression during cell wall biogenesis, whereby the WALLDOF transcription factor would only be modulated in the organ(s) or tissue(s) or cell type(s) in which its action is required. As used here, "xylem-preferred promoter" means that the nucleic acid molecules disclosed herein are more active in the xylem than in any other plant tissue. Xylem-preferred promoters that could be used include, but are not limited to, the xylem-preferred coumarate-4-hydroxylase (C4H) gene promoter, the xylem-preferred tubulin (TUB) gene promoter, and the xylem-preferred lipid transfer protein (LTP) gene promoter. Other suitable xylem-preferred promoters are disclosed in WO 2005/096805, supra.

A construct may also contain termination sequences, which are positioned downstream of the nucleic acid molecules disclosed herein, such that transcription of mRNA is terminated, and polyA sequences added. Exemplary of such terminators are the cauliflower mosaic virus (CaMV) 35S terminator and the nopaline synthase gene (TNOS) terminator. The construct also may contain enhancers, start codons, splicing signal sequences, and targeting sequences.

A construct may optionally contain a selection marker by which transformed cells can be identified in culture. The marker may be associated with the heterologous nucleic acid molecule, i.e., the gene operably linked to a promoter. As used here, the term "marker" refers to a gene encoding a trait or a phenotype that permits the selection of, or the screening for, a plant or cell containing the marker. In plants, for example, the marker gene may encode antibiotic or herbicide resistance. This allows for selection of transformed cells from among cells that are not transformed or transfected.

Examples of suitable selectable markers include without limitation adenosine deaminase, dihydrofolate reductase, hygromycin-β-phosphotransferase, thymidne kinase, xanthine-guanine phospho-ribosyltransferase, glyphosate and glufosinate resistance, and amino-glycoside 3'-O-phosphotransferase (kanamycin, neomycin and G418 resistance). These markers may include resistance to G418, hygromycin, bleomycin, kanamycin, and gentamicin. The construct also may contain the selectable marker gene Bar, which confers resistance to herbicidal phosphinothricin analogs like ammonium gluphosinate. Thompson et al., *EMBO J.* 9: 2519-23 (1987). Other suitable selection markers are known as well.

Visible markers such as green florescent protein (GFP) may be used. Methods for identifying or selecting transformed plants based on the control of cell division have also been described. See WO 2000/052168 and WO 2001/059086.

Replication sequences, of bacterial or viral origin, may also be included to allow the construct to be cloned in a bacterial or phage host. Preferably, a broad host range prokaryotic origin of replication is used. A selectable marker for bacteria may be included to allow selection of bacterial cells bearing the desired construct. Suitable prokaryotic selectable markers also include resistance to antibiotics such as kanamycin or tetracycline.

Other nucleic acid sequences encoding additional functions may also be present in the construct, as is known in the art. For instance, when *Agrobacterium* is the host, T-DNA sequences may be included to facilitate the subsequent transfer to and incorporation into plant chromosomes.

Plants for Genetic Engineering

The present disclosure entails the genetic manipulation of plants for increasing cell wall deposition and/or biomass density, via modulation a polynucleotide sequence that encodes WALLDOF.

In this regard plants include without limitation *Eucalyptus* ssp, *Poplar* ssp, conifers, willow, sugarcane, sorghum, wheat, corn, cotton, soybean, alfalfa, vegetables (including but not limited to broccoli, cauliflower, cabbage, radish, Chinese cabbage, onion, carrot, cucumber, pepper, tomato, eggplant, squash, gourds, pumpkin, okra, spinach, dry bean, pea, leek, lettuce, fennel, garden bean, sugar beets, etc.), melons, watermelons, canola (rapeseed), rice, barley, peanut, pigeon pea, millet, grape, berries (including but not limited to blue, black, raspberry, mulberry, cranberry, boisen berry, etc.), fruits from trees (including but not limited to plum, peach, nectarine, apricot, kiwi, pomegranate, mango, fig, orange, lemon, lime, blood orange, grapefruit, apple, banana, and the like), nut trees (cocounut, walnut (English and black), pecan, almond, hazelnut, Brazil nut, hickory nut, acorn), oilseed producing plants (including but not limited to sunflower, rapeseed, etc.) sudan grass, miscanthus, switchgrass, elephant grass, and fountain grass, among others. However, the list is not in any way limiting, as other types of plants will be known to those of skill in the art and could be used for increasing cell deposition and biomass.

The present invention is particular useful to engineer plants for a variety of industries and applications including but not limited to for the pulp and paper industry and the bioenergy industry, general forestry, biomass feedstock, biomaterials for bioenergy, cereals, beverages, confectionaries, sugars and sweeteners; fibers; dyes; tannins; paints; resins; latexes, hydrogels, paints, oils, waxes, perfumes, floral and ornamentals, food colorings, spices, herbs, medicinals, pharmaceuticals, nutraceuticals, bamboo, cork, and wood.

Genetically manipulation encompasses any methodology for introducing a nucleic acid into a host organism or otherwise modifying genetic expression of the organism. For example, a plant is genetically modified when it is transformed with a polynucleotide sequence that increases expression of a gene, such as walldof, and thereby increases cell wall deposition and biomass density. In contrast, a plant that is not transformed with a polynucleotide sequence is a control plant and is referred to as a "non-transformed" plant.

In certain embodiments, genetically modified plants are selected that have the DNA construct incorporating the walldof gene in its genome. As an example, a transgenic poplar plant so transformed are distinguished from a non-transformed poplar plant by the fact that they comprise at least one copy of the nucleic acid molecule set for in SEQ ID NO: 1 stably integrated into their genome in addition to copies of such a molecule which occur naturally in the non-transformed poplar plant.

"Plant" is a term that encompasses whole plants, plant organs (e.g. leaves, stems, roots, etc.), seeds, differentiated or undifferentiated plant cells, and progeny of the same. Plant material includes, without limitation, seeds suspension cultures, embryos, meristematic regions, callus tissues, leaves, roots, shoots, stems, fruit, gametophytes, sporophytes, pollen, and microspores. The class of plants which can be used is generally as broad as the class of higher plants amenable to genetic engineering techniques, including angiosperms, both monocotyledonous and dicotyledonous plants, as well as gymnosperms. The term also denotes any cellulosic plant material that can be genetically manipulated, including but not limited to differentiated or undifferentiated plant cells, protoplasts, whole plants, plant tissues, or plant organs, or any component of a plant such as a leaf, stem, root, bud, tuber, fruit, rhizome, or the like. As used here, "propagule" includes a structure with the capacity to give rise to a new plant, e.g., a seed, a spore, or a part of the vegetative body capable of independent growth if detached from the parent.

In this description, the term "bioenergy" denotes useful, renewable energy produced from organic matter, the conversion of complex carbohydrates of organic matter into energy. Organic matter may either be used directly as a fuel, burned as is to produce electricity, processed into liquids and gasses, or be a residual of processing and conversion.

The term "biomass" means any organic matter that is available on a renewable or recurring basis, including agricultural (i.e. food and fiber) crops and trees, wood and wood residues, plants (including aquatic plants), grasses and other residue materials. Biomass is generally produced in a sustainable manner from water, mineral nutrients and carbon dioxide by photosynthesis.

An increase in biomass or biomass density can be seen by an increase in at least one of plant phenotype including but not limited to height; weight, size or numbers of leaves; length and thickness of shoots; length, thickness and branching of roots; seed production per plant; flowering; numbers and sizes of cells in tissues, including wood-forming tissues; and development of plant reproductive organs.

Illustrative Methods for Genetic Modification

A polynucleotide sequence, such as a walldof DNA sequence, may be stably integrated into a plant genome in various ways known to the art. Both monocotyledonous and dicotyledonous angiosperm or gymnosperm plant cells may be transformed. For example, see Klein et al., *Biotechnology* 4: 583-590 (1993); Bechtold et al., *C. R. Acad. Sci. Paris* 316:1194-1199 (1993); Bent et al., *Mol. Gen. Genet.* 204: 383-396 (1986); Paszowski et al., *EMBO J.* 3: 2717-2722 (1984); Sagi et al., *Plant Cell Rep.* 13: 26 15-286 (1994). *Agrobacterium* species such as *A. tumefaciens* and *A. rhizogenes* can be used, for example, in accordance with Nagel et al., *Microbiol Lett* 67: 325 (1990). Additionally, plants may be transformed by *Rhizobium, Sinorhizobium* or *Mesorhizobium* transformation. Broothaerts et al., *Nature* 433:629-633 (2005).

Additional methods for genetically modify a plant or cell include, but are not limited to, electroporation, particle gun bombardment (Klein et al. (1987) *Nature.* 327:70-73), calcium phosphate precipitation, and polyethylene glycol fusion, transfer into germinating pollen grains, direct transformation (Lorz et al., *Mol. Genet.* 199: 179-182 (1985)), and other methods known to the art. If a selection marker, such as kanamycin resistance, is employed, it makes it easier to determine which cells have been successfully transformed. Marker genes may be included within pairs of recombination sites recognized by specific recombinases such as cre or flp to facilitate removal of the marker after selection. See U.S. published application No. 2004/0143874.

For the purposes of this description, a walldof DNA sequence operably linked to a promoter may be introduced into a plant or cell. For example, an illustrative construct may comprise a walldof sequence operably linked to a xylem-preferred promoter.

Plant Transformation

The present disclosure comprises the genetic manipulation of plants, especially plants mentioned supra or any plant useful for any industry or application described supra, to increase cell wall deposition and/or biomass density.

The phrase "transgenic plant" refers to a plant that comprises a nucleic acid sequence that is also present per se in another organism or species or that is optimized, relative to host codon usage, from another organism or species. Both monocotyledonous and dicotyledonous angiosperm or gymnosperm plant cells may be transformed in various ways known to the art. For example, see Klein et al., *Biotechnology* 4: 583-90 (1993); Bechtold et al., *C. R. Acad. Sci. Paris* 316: 1194-99 (1993); Bent et al., *Mol. Gen. Genet.* 204: 383-96 (1986); Paszowski et al., *EMBO J.* 3: 2717-22 (1984); Sagi et al., *Plant Cell Rep.* 13: 262-66 (1994). *Agrobacterium* species such as *A. tumefaciens* and *A. rhizogenes* can be used in accordance with Nagel et al., *Microbiol Lett* 67: 325 (1990), for example. Additionally, plants may be transformed by *Rhizobium, Sinorhizobium* or *Mesorhizobium* transformation. Broothaerts et al., *Nature* 433: 629-33 (2005). Also, the phrase "transgenic plant" refers to a plant that has incorporated a DNA sequence, including but not limited to genes that are not normally present in a host plant genome, DNA sequences not normally transcribed into RNA or translated into a protein ("expressed"), or any other genes or DNA sequences that one desires to introduce into the non-transformed plant, such as genes that normally may be present in the non-transformed plant but that one desires either to engineer genetically or to have altered expression. The "transgenic plant" category includes both a primary transformant and a plant that includes a transformant in its lineage, e.g., by way of standard introgression or another breeding procedure.

For example, *Agrobacterium* may be transformed with a plant expression vector via electroporation, for example, after which the *Agrobacterium* mediates the introduction of the expression vector into a plant cells. Additional methods for accomplishing this include but are not limited to electroporation, particle gun bombardment, calcium phosphate precipitation, and polyethylene glycol fusion, transfer into germinating pollen grains, direct transformation, Lorz et al., *Mol. Genet.* 199: 179-82 (1985), and other known techniques. If a selection marker, such as kanamycin resistance, is employed, it makes it easier to determine which cells have been successfully transformed. Marker genes may be included within pairs of recombination sites recognized by specific recombinases, such as cre or flp, to facilitate removal of the marker after selection. See U.S. published application No. 2004/0143874.

Transgenic plants without marker genes may be produced using a second plasmid comprising a nucleic acid encoding the marker, distinct from a first plasmid that comprises a walldof DNA sequence. The first and second plasmids or portions thereof are introduced into the same plant cell, such that the selectable marker gene that is transiently expressed, transformed plant cells are identified, and transformed plants are obtained in which the walldof DNA sequence is stably integrated into the genome and the selectable marker gene is not stably integrated. See U.S. published application No. 2003/0221213. Transgenic plants also may be produced without selectable markers, as the plants can be analyzed by various methods including without limitation PCR and DNA sequencing.

The *Agrobacterium* transformation methods discussed above are known to be useful for transforming dicots. Additionally, de la Pena et al., *Nature* 325: 274-76 (1987), Rhodes et al., *Science* 240: 204-07 (1988), and Shimamato et al., *Nature* 328: 274-76 (1989), document methodology for using *Agrobacterium* to transform cereal monocots. Also, see Bechtold et al., *Methods Mol Biol.* 82: 259-66 (1998), illustrating vacuum infiltration for *Agrobacterium*-mediated transformation.

Plant cells may be transformed with a nucleic acid construct disclosed herein without the use of a selectable or visible marker and transgenic organisms may be identified by detecting the presence of the introduced construct. The presence of a protein, polypeptide, or nucleic acid molecule in a particular cell can be measured to determine if, for example, a cell has been successfully transformed or transfected. For example, and as routine in the art, the presence of the introduced construct can be detected by PCR or other suitable methods for detecting a specific nucleic acid or polypeptide sequence. Additionally, transformed cells may be identified by recognizing differences in the growth rate or a morphological feature of a transformed cell compared to the growth rate or a morphological feature of a non-transformed cell that is cultured under similar conditions. See WO 2004/076625.

Methods of regenerating a transgenic plant from a transformed cell or culture vary according to the plant species but are based on known methodology. For example, methods for regenerating of transgenic *Nicotiana* and *Eucalyptus* plants are well-known.

Selection and Analysis of Genetically Modified Plants

Genetically modified plants are selected that have modulated expression of walldof gene relative to a non-transgenic plant of the same species. Additionally, various embodiments of the inventive genetically modified plants may have increased cell wall deposition and biomass density. For example, an inventive transgenic plant may have a phenotype characterized by (1) an increased cell wall deposition as visualized and measured by histochemical analysis (2) an altered wall area and percentage of wall area over the total cell area such that biomass density is increased because wall area and percentage of wall area are positively correlated with biomass density.

The phrase "modulated expression" refers to modulating the level of the WALLDOF transcription factor comprising an amino acid sequence set forth in SEQ ID NO: 2 at levels from 10 to 50% higher that of the endogenous regulatory polypeptide, preferably from 30 to 80% higher that of the endogenous regulatory polypeptide, most preferably from 50 to 150% higher that of the endogenous regulatory polypeptide, most preferably from 70 to 200% higher that of the endogenous regulatory polypeptide, most preferably 100 to 300% higher that of the endogenous regulatory polypeptide. Plants, plant cell, and plant parts having the expression cassette also are provided.

The phrase "cell wall deposition," refers to the construction and biosynthesis of a plant cell wall through deposition of structural or non-structural molecules. More particularly, the molecules deposited for cell wall biosynthesis comprises celluloses, hemicelluloses, pectic polysaccharides, proteins, lignins, suberins, wax and cutin, but is not any way limiting to those. The phrase "cell wall deposition" also refers to both primary and secondary cell wall synthesis at any plant cells or tissues or organs, which includes but is not limited to xylem, phloem, parenchyma, meristems as well as cambium, root, stem, leaf, seed, flower buds, among any others.

The phrase "increased cell wall deposition" refers to a quantitative increase of cell wall thickness so that cell wall area and percentage of wall area over the total cell area can be increased from at least 10 to 50% preferably from at least 30 to 80%, most preferably from at least 50 to 150%, most preferably from at least 70 to 200%, most preferably from at least 100 to 300% of the cell wall area and percentage of wall area over the total cell area of a non-transformed plant.

The phrase "increased biomass density" refers to a quantitative increase of biomass density relative to a non-transformed plant of the same species. The biomass density of an engineered plant as provided herein can be increased from at least 10 to 50% preferably from at least 30 to 80%, most preferably from at least 50 to 150%, most preferably form at least 70 to 200%, most preferably from at least 100 to 300% of the biomass density of a non-transformed plant.

Methods for Quantifying Increased Cell Wall Deposition

Genetically modified plants provided herein may be characterized by an increased cell wall deposition. This is achieved by modulating the expression of a walldof gene. Modulating walldof gene expression in a plant or plant cell is achieved by incorporating in a nucleic acid construct a promoter such as the ones cited supra that shows a tissue preferred expression. It is also an embodiment to generate transgenic plants that express WALLDOF protein, preferably under the control of different promoters, such as other tissue-specific promoters or constitutive promoters. The increased cell wall deposition is achieved by expressing a suitable amount of WALLDOF protein at a suitable time and location. Such fine-tuning may be done by determining the most appropriate promoter and also by selecting transgenic "events" that show the desired expression level.

Transformed plants expressing desired levels of WALLDOF protein are selected by e.g. analyzing the copy number (Southern blot analysis), mRNA transcript levels (e.g. RT-PCR using specific walldof DNA sequence primer pairs or flanking primers) or by analyzing the presence and level of WALLDOF proteins in various tissues (e.g. SDS-PAGE; ELISA assays, etc). High or moderate WALLDOF-expressing events are selected for further tests until a high performing elite event with a stable integrated walldof DNA construct is obtained.

Whole plants, seeds, cells, tissues and progeny (such as F1 hybrids, F2 seeds/plants, etc.) of any of the transformed plants described above are encompassed here and can be identified by the presence of the transgene in the DNA, as determined, for example, by PCR analysis using total genomic DNA as template and using walldof-specific PCR primer pairs. Also "event specific" PCR diagnostic methods can be developed, where the PCR primers are based on the plant DNA flanking the inserted chimeric gene, see U.S. Pat. No. 6,563,026. Similarly, event-specific AFLP fingerprints or RFLP fingerprints may be developed that identify the transgenic plant or any plant, seed, tissue or cells derived therefrom.

It is understood that the transgenic plants provided herein preferably do not show non-desired phenotypes, such as yield reduction, enhanced susceptibility to diseases (especially to necrotrophs) or undesired architectural changes (dwarfing, deformations) etc. and that, if such phenotypes are seen in the primary transformants, these can be removed by breeding and selection methods (crossing/backcrossing/selfing, etc.). Any of the transgenic plants described herein may be homozygous or hemizygous for the transgene.

Increased cell wall deposition can be determined by the analysis of histological sections of biological materials such as the wood xylem. In general the analysis is performed in the stem that can be cross-sectioned at for example 10 μm thick, stained with toluidine blue and observed under a light microscope. Measurements of the wall area per cell can be done using the ImageTools software.

Methods for Quantifying Increased Biomass Density

The increase in cell wall deposition results in an increase of apparent biomass density. Biomass density can be determined by any suitable method. As an example there is the X-ray methodology that consists in cutting stem discs of 1 mm thickness and subject these discs to x-ray diffraction. Radiographs obtained from stem discs are scanned and measured using digital image software as described, for example, by Mothe et al., *Ann. For. Sci.*, 55: 301-13 (1998).

Specific examples of methods for obtaining transgenic plants expressing walldof gene as well as methods for evaluating the phenotypic effect of the gene are presented. They are meant to be exemplary and non-limiting.

EXAMPLE 1

Identification of Walldof Gene in Poplar

To develop the methods and make the DNA constructs of the present invention firstly we searched for transcription factors that are preferred expressed in the poplar xylem.

The collection of over 400,000 ESTs from *Populus* sp. available in GenBank was searched for the tissue-specific pattern of expressed genes. For this purpose the cDNA libraries made from different poplar tissues, were grouped into representative tissues: suspension cell, apical shoot, bark, cambium, seed, wood, flower bud, leaf and root. A set of clusters generated by the CAP3 program (Huang and Madan, *Genome Res.*, 9:868-877, 1999) was searched for those composed of at least 90% of EST reads from libraries representing poplar cambium and wood tissues. Additionally, the clusters was searched for those composed of at least three EST reads from cambium and wood tissues and preferably less than two reads from other libraries.

The selected clusters were then aligned, using the Blast-X algorithm with a cut off e-value<=1e$^{-5}$ (Altschul et al., *Nucleic Acids Res.*, 25:3389-3402, 1997), to sequences from a curated *Arabidopsis thaliana* transcription factor database composed of sequences obtained from the *Arabidopsis* Gene Regulator Information Server (AGRIS) AtTFDB database. The results were stored in a local database of *Populus* sp. transcription factors and browsed via a web-based interface to filter specific transcription factor sequences of genes expressed specifically or preferably in the cambium and/or wood tissues of *Populus* sp.

Figure 1:
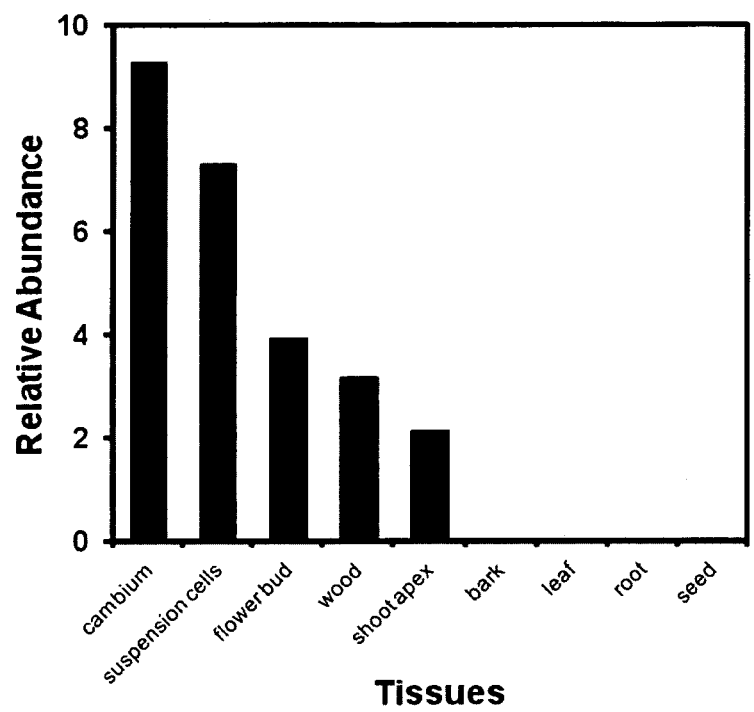
FIG. 1 shows differential expression of walldof gene in different poplar tissues.

Among a group of transcription factors that were expressed at a cambium and/or wood preferred manner, one cluster representing a DOF transcription factor family member with a cambium-preferred expression profiling was found (FIG. 1). The EST representing this DOF transcription factor contained a 768-bp open reading frame 99% identical to the open reading frame of *Populus trichocarpa* gene model estExt_fgenesh4_pg.C_LG_XV0093. Because of its association with cell wall deposition, we named it WALLDOF (for wall-associated DOF domain protein).

EXAMPLE 2

Identification of Walldof Homologs in Poplar and Other Plants

According to a phylogenetic study WALLDOF is part of a cluster or Glade comprised of Ptr_DOF40, Ptr_DOF02, PTR_DOF06, Ptr_DOF15, Ptr_DOF25, Os02g45200 (NCBI ID: Os02g0673700), Os04g47990 (NCBI ID: Os04g0567800), Os02g15350 (NCBI ID: Os02g0252400), AT2G46590, AT3G61850, AT4G24060, AT1G64620, and AT4G00940. Yang et al., *Plant Physiol.*, 142: 820-30 (2006).

By sequence similarity analysis, determined via a BLAST search, for example, other sequences of other plants are identified: two from grape genome (*Vitis vinifera*—Phtozome/JGI ID GSVIVT00037222001 and GSVIVT00006675001), two from soybean genome (*Glycine max*—GenBank annotation ID DOF21-gi|112363396|gb|ABI16022.1|- and DOF28-gi|112363398|gb|ABI16023.1|). Within other grasses, two sorghum putative DOF genes (JGI ID Sb04g032040.1 and Sb06g025680.1) are similar to WALLDOF. It is possible to identify two similar DOFs in the current assembly of the maize genome (Tigr AZM5): DOF1 comes from the contig AZM5_18231 and DOF2 comes from the contig AZM5_4711.

Figure 2:
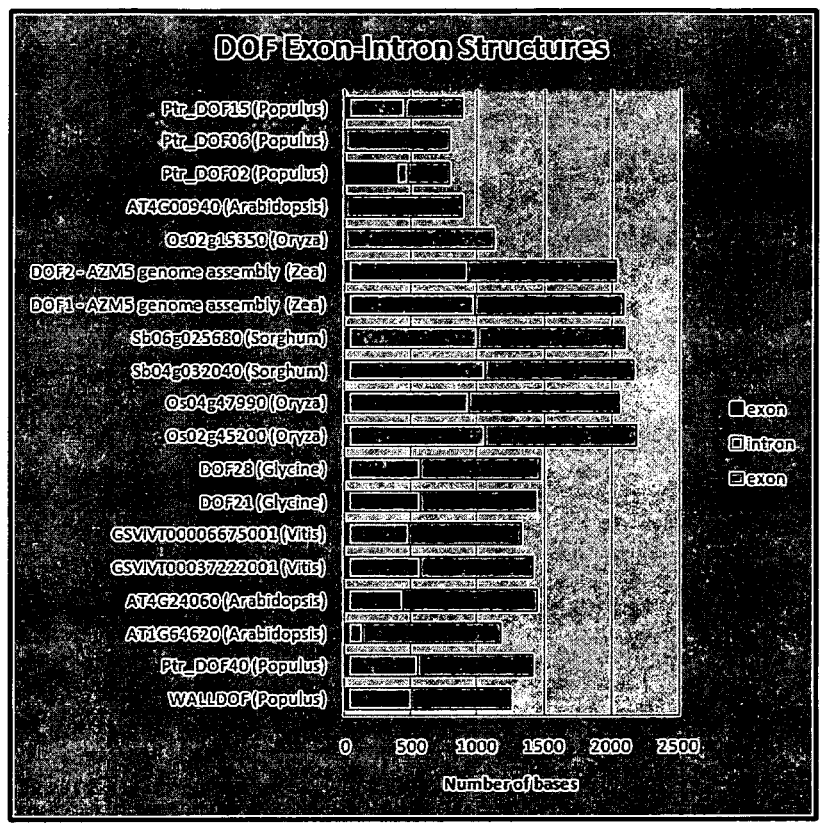
FIG. 2 shows the structure in terms of intron-exon structure of putative WALLDOF homologs.

Besides sequence and phylogenetic similarity, the above walldof-similar genes share similar intron-exon structures as well as common conserved protein domains. FIG. 2 shows the similarities in terms of intron-exon structure (inside the coding region). Similar walldof genes present a structure composed of two exons, except Ptr_DOF06, Ptr_DOF25, AT4G00940, and Os02g15350.

In order to analyze putative motifs related to above WALLDOF-similar members, we have analyzed alignment of dicotyledons and monocotyledons separately. FIG. 3 shows the similarity among dicots and FIG. 4 shows the similarity among monocots. Both alignments sets, when analyzed together, resulted in the motifs described in FIG. 5. This is an indication that putative WALLDOF-similar members from different species, which are encoded by "paralog" genes, as defined above, share these common motifs in their protein sequence.

EXAMPLE 3

Isolation and Cloning of Walldof from *Populus deltoides*

(a) Preparation of mRNA from *Populus deltoides* Cambium/Xylem and cDNA Synthesis:

Bark was removed from stem cuttings of one-year-old *Populus deltoides* trees. The inner part of the stem, containing cambium, xylem and pith, was cut in small pieces, frozen in liquid nitrogen and used for RNA extraction using the cetyl-trimethyl-ammonium bromide (CTAB) extraction method. See Aldrich and Cullis, *Plant Mol. Biol. Report.*, 11: 128-41 (1993). cDNA was synthesized using total RNA as template. The first strand of cDNA was produced by RT-PCR using Superscript II reverse transcriptase (Invitrogen) and an oligo (dT) primer. Double-stranded cDNA was obtained by the subsequent polymerase reaction, using gene-specific primers, as described below.

(b) Design of PCR Primers and RT-PCR Reaction:

Oligomers based on *Populus trichocarpa* gene model estExt_fgenesh4_pg.C_LG_XV0093 were synthesized as primers for PCR, including either the region around the first ATG codon or around the termination codon of the main ORF encoding the polypeptide to amplify the entire coding region of the main ORF. The sequences of the primers were:

```
DOFNCO
                                 (SEQ. ID. NO: 3)
5'-ATCCATGGATACTTCTACTCAGTGGCCACAGG-3'

DOFXBA
                                 (SEQ. ID. NO: 4)
5'-ACTCTAGATTACCATGATCCACCACCTAACATTC-3'
```

The cDNA pool obtained in (a) was used as the template in a PCR reaction with the primers of SEQ. ID. NOs: 3 and 4. The PCR involved 40 cycles of 1 minute at 94° C., 1 minute at 51° C., and 2 minutes at 72° C. followed by an extra step of elongation at 72° C. for 7 minutes. The PCR products were isolated by gel electrophoresis on 1.0% agarose followed by ethidium bromide staining of the electrophoresed gel and detection of amplified bands on a UV transilluminator. The detected amplified band was verified and cut out of the agarose gel with a razor. The pieces of gel were transferred to 1.5 mL microtubes, and the DNA fragments were isolated and purified using a GFX PCR clean up and gel band purification kit (Amersham). The recovered DNA fragments were subcloned in a commercially available cloning vector, transformed into *E. coli*, and then used to prepare plasmid DNA, which was then sequenced by the dideoxy method, using standard protocols. See Messing, *Methods in Enzymol.*, 101: 20-78 (1983). The resultant nucleotide sequence, set forth in SEQ. ID. NO: 1, encodes the WALLDOF polypeptide identified here with SEQ. ID. NO: 2.

EXAMPLE 4

*Agrobacterium*-Mediated Transformation of *P. tremula×P. alba* Hybrid

The nucleic acid molecule isolated from *Populus deltoides* and obtained in Example 2 was cloned into an expression vector downstream of a xylem-preferred coumarate-4-hydroxylase gene (C4H) promoter, as described in WO 2005/096805 (FIG. 6). The resulting expression construct was amplified in *E. coli*, and then transformed into the *Agrobacterium tumefaciens* LBA4404 strain.

Wild-type aspen hybrid (*Populus tremula×Populus alba*) was transformed with *Agrobacterium tumefaciens* carrying the construct obtained in Example 3. Petioles and intermodal stem segments from in vitro micropropagated plants were used as explants. Transformed shoots were selected on regeneration medium containing 100 mg/L of kanamycin and allowed to root on the Murashige and Skoog medium. Selected plants were subsequently transferred to soil and grown in the greenhouse.

Transgenic events were verified by PCR. Integration of the gene construct in the genome of the transgenic plants was confirmed by PCR analysis of the selectable marker gene (kanamycin) and the walldof gene.

EXAMPLE 5

Overexpression of Walldof Increases Cell Wall Deposition in Transgenic Poplar

Histological analysis of xylem were performed in the lower part of the stem of two months old poplar trees transformed with the construct obtained in Example 3. Stem sections were cross-sectioned (10 μm thick) from wild type and transgenic lines with a microtome (LEICA RM2255) equipped with a steel knife. The sections were subjected to toluidine blue staining and observed under a light microscope.

Figure 7:
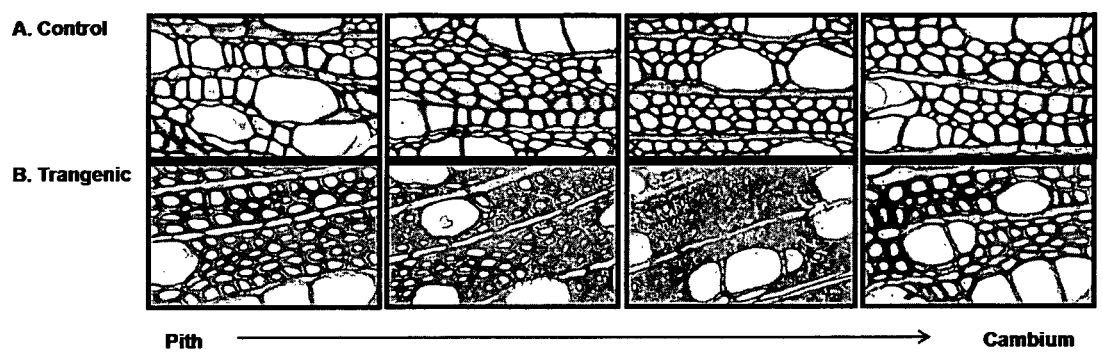
FIG. 7 shows stem sections (base level) across the xylem of a control plant (A) and a transgenic event (B) transformed with the plant expression plasmidial vector pALELLYX-DOF of the invention stained with toluidine blue dye.
Figure 8:
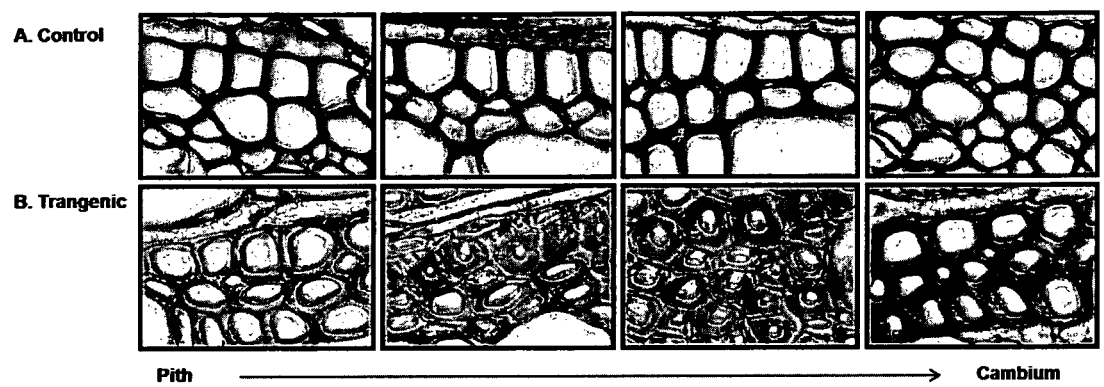
FIG. 8 shows a high magnification stem sections (base level) of one control plant (A) and one transgenic line (B) of *Populus tremula×Populus alba* transformed with the plant expression cassette pALELLYX-DOF of the invention. Sections stained with toluidine blue dye shows the increased cell wall deposition of the transgenic lines when compared with non-transformed control plants.

FIG. 7 shows stem sections across the xylem, from pith to cambium, of a non-transformed plant (A) and a transgenic event transformed with the construct obtained in Example 2 (B). It is possible to see that the thickness of the cell wall has dramatically increased in the transgenic event when compared to the non-transformed plant. This shows clearly a dramatic enhancement of cell wall deposition caused by the modulated expression of walldof in the transformed event. Also, there is a marked decrease in the lumen width of cells in the transformed event. FIG. 8 presents a higher magnification of a stem cross-section of the same transformed event shown in FIG. 6 compared to a non-transformed plant. It can be clearly observe a marked decrease in the lumen width as a consequence of the increased thickness of the cell wall.

Figure 9:
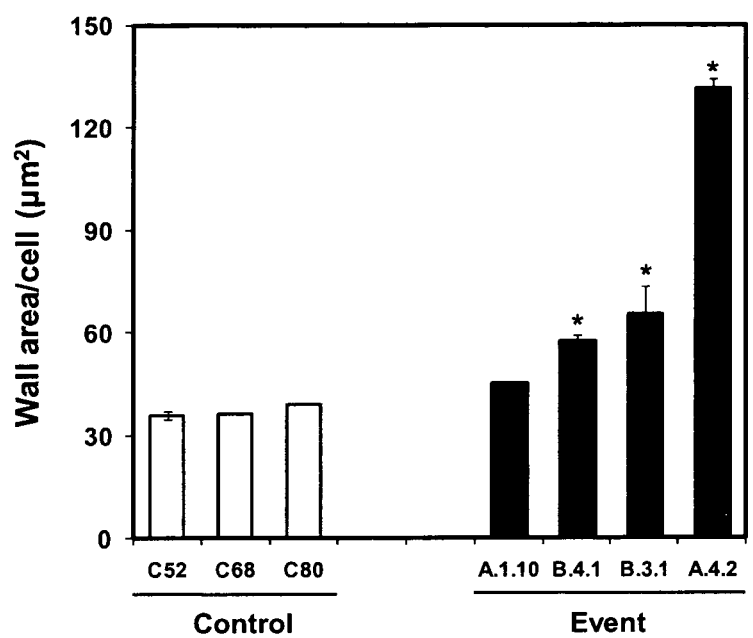
FIG. 9 shows the wall area per cell ($\mu m^2$) of four transgenic lines transformed with the plant expression plasmidial vector pALELLYX-DOF of the invention and three control plants (mean of three plant replicates). Asterisk denotes transgenic lines having statistically significant increased wall area over the non-transgenic control plants according to Student's test.

Measurements of the wall area of the cell indicated a dramatic thickening of cell walls in replicates of the transformed events. Events A.4.2, B.3.1 and B.4.1 presented an increase in the wall area per cell of 255%, 77% and 55%, respectively, when compared to non-transformed plants (FIG. 9).

Figure 10:
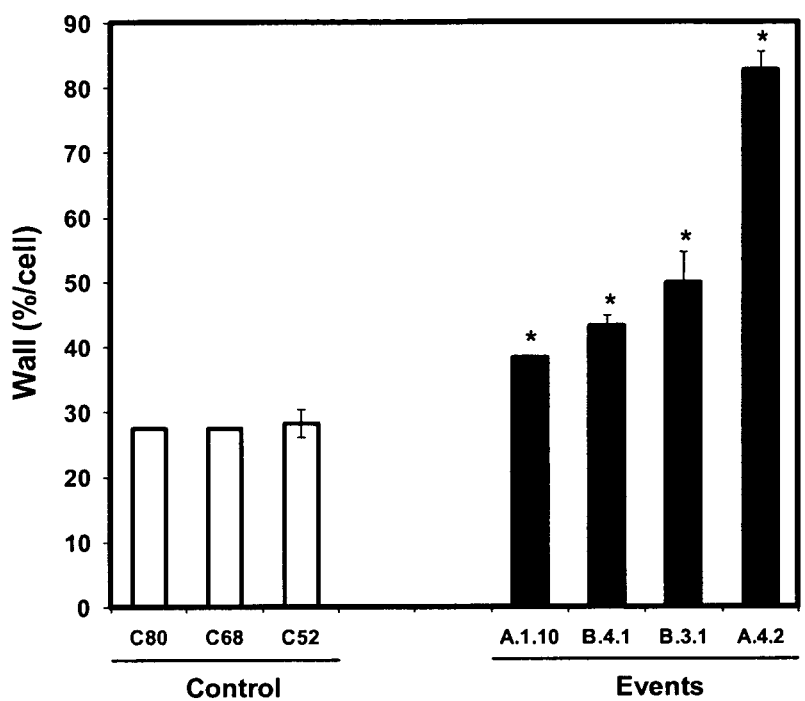
FIG. 10 shows the percentage of cell area occupied by the wall of four transgenic lines transformed with the plant expression plasmidial vector pALELLYX-DOF of the invention and three control plants (mean of three plant replicates). Asterisk denotes transgenic lines having statistically significant increased percentage of cell wall per cell over the non-transgenic control plants according to Student's test.

The percentage wall area over the total cell area was significantly increased in the transformed plants varying from 38% to 82% compared to the 27% over the total cell area of the non-transformed control plants (FIG. 10).

EXAMPLE 6

Overexpression of Walldof Increases Apparent Wood Density in Poplar

The increase in cell wall deposition resulted in an increase in the apparent wood density of transformed plants. For the apparent wood density determination, samples (1 mm thickness) from the stem lower part were cut using a twin-blade saw. The thin laths at 12% moisture content (MC) were x-rayed using a Hewlett Pakard Faxitron (Model 43805 N) previously adjusted (time: 5 minutes; energy: 16 Kv; intensity: 3 mA). The films (Kodak, Diagnostic Film X-Omat XK1, 24×18 cm) were developed using normal procedures. The radiographs of transformed and non transformed plants were scanned in a 256 gray scale with 1,000 dpi resolution. Measurements of x-ray micro-density (x-ray densitometry) were made on this digital image by CERD software. Mothe et al., *Ann. For. Sci.*, 55: 301-13 (1998). A methodology for densitometry profiles, described by Walker and Doob, *Wood Fiber Sci.*, 20: 35-43 (1998), was used for determining the mean apparent wood density.

Figure 11:
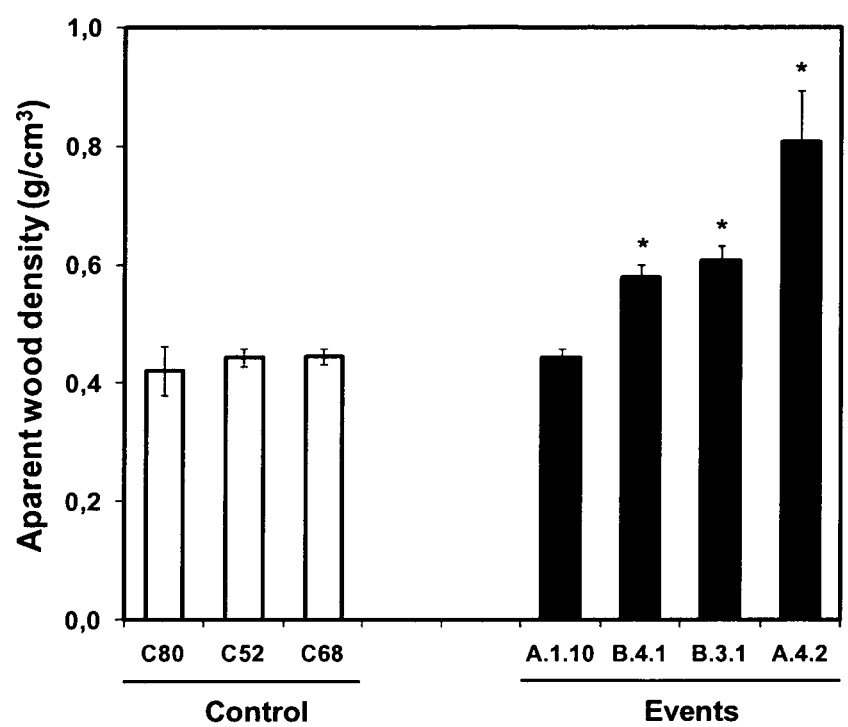
FIG. 11 shows the apparent wood density (g/cm$^3$) of four transgenic lines transformed with the plant expression plasmidial vector pALELLYX-DOF of the invention and three control plants (mean of three plant replicates). Asterisk denotes transgenic lines having statistically significant increased in wood density over the non-transgenic control plants according to Student's test.
Figure 12:
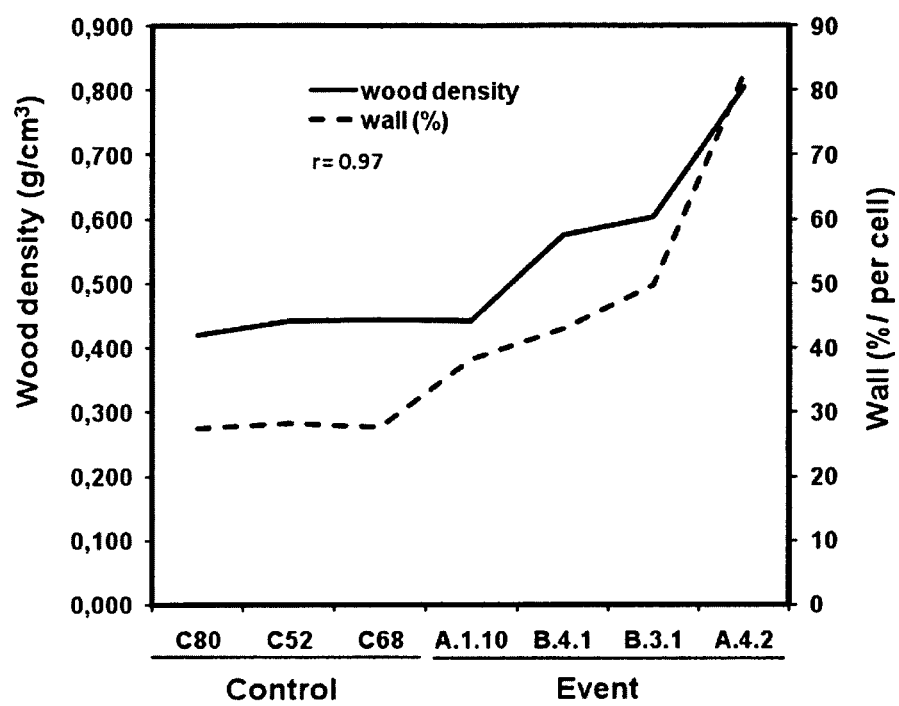
FIG. 12 shows the positive correlations between the apparent wood density (g/cm$^3$) and the percentage of cell area (%/per cell) occupied by the wall.

Events A.4.2, B.3.1 and B.4.1 showed an increase of 84%, 38% and 32% in the apparent wood density, respectively, when compared to non-transformed plants (FIG. 11). Poplar is considered a soft wood plant with a wood density around 300 to 400 g/cm$^3$. The transformed events of the invention showed wood density of around 0.66 g/cm$^3$ in events B.3.1 and B4.1, and about 0.82 g/cm$^3$ in event A.4.2 as compared to the a wood density of around 0.42 g/cm$^3$ in the non-transformed plants (FIG. 11). The increased cell wall deposition greatly contributes to the wood density results, since the correlation between these two attributes was shown to be 0.97 (FIG. 12).

EXAMPLE 7

Increased Cell Wall Deposition Correlates with Increased Walldof Expression

To determine the abundance of walldof transcripts and to correlate the level of walldof expression with the intensity of the phenotype observed, we performed quantitative reverse transcription-polymerase chain reaction (qRT-PCR) using RNA isolated from developing xylem of non-transformed poplar plants and the four transformed events analyzed as described above. Liquid N2-frozen tissue was ground to powder with mortar and pestle, and total RNA was isolated using the cetyltrimethyl-ammonium bromide (CTAB) extraction method (Aldrich and Cullis, *Plant Mol. Biol. Report.*, 11:128-141, 1993). Total RNA was treated with DNaseI (Promega), and cDNA first strand was synthesized with Superscript II Reverse Transcriptase (Invitrogen) using 1 μg of total RNA. One tenth of the cDNA was used in combination with gene specific primers at 500 nM concentration and SYBR Green PCR Master Mix (Applied Biosystems). PCR was performed on an ABI Prism 7000 Sequence Detection System (Applied Biosystems). For amplification of walldof transcripts, oligonucleotide primers walldof Fwd (5'-TGCAAGAAT-TCAAGCCATC-3') (SEQ ID NO:7) and WALLDOF Rev (5'-GCAGCAGGTTCCAAGTAATG-3') (SEQ ID NO:8) were used. *Populus trichocarpa* actin gene sequence (estext_genewisel_V1.C__1850029), used as a reference gene to normalize template amounts, was amplified with the following oligonucleotide primers ACTIN Fwd (5'-GCT-GTCCTTTCCCTGTATGC-3') (SEQ ID NO:9) and ACTIN Rev (5'-ACGACCAGCAAGATCCAAAC-3') (SEQ ID NO:10). Amplification was performed at 50° C. for 2 min, 95° C. for 10 min, and 45 cycles at 95° C. for 15 sec and 60° C. for 1 min. The specificity of the amplification reaction was evaluated by the analysis of the dissociation curves. The ratio between the amounts of the walldof and ACTIN amplified products was calculated using the $2^{-\Delta\Delta Ct}$ method (Livak and Schmittgen, *Methods*, 25:402-408, 2001). walldof transcript levels relative to those of ACTIN were calculated as the average of values obtained from three independent samples used as biological replicates.

The transgenic events that presented an increase in cell wall deposition and in apparent wood density had a higher walldof gene expression level in stem when compared to non-transformed plants. The higher the walldof gene expression level the stronger the phenotypes related to cell wall deposition and wood density.

Figure 13:
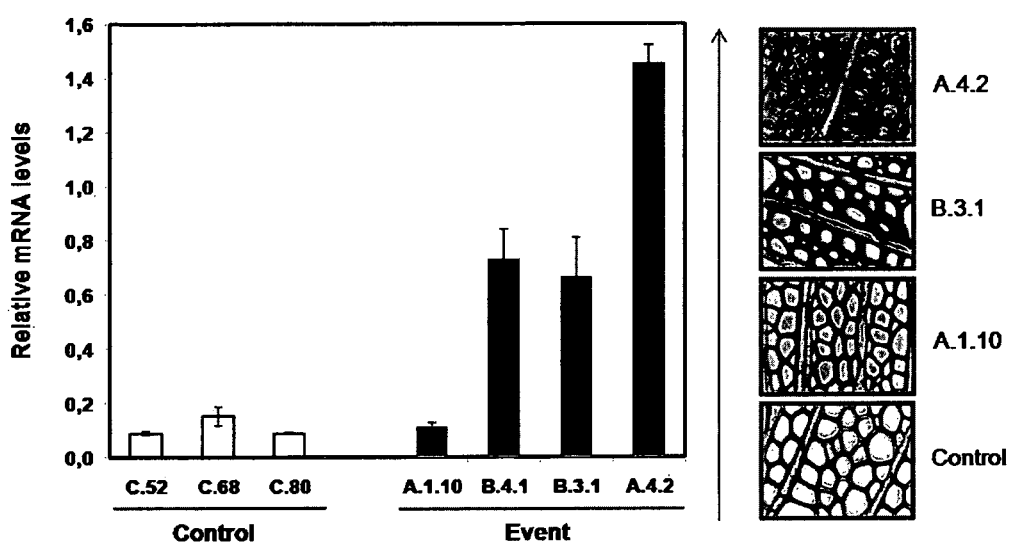
FIG. 13 shows the walldof relative mRNA levels in developing xylem of four transgenic lines transformed with the plant expression plasmidial vector pALELLYX-DOF of the invention and three control plants (mean of three plant replicates).

Event A.4.2, which showed the highest apparent wood density and cell wall deposition, presented an increase of 14-fold in walldof gene expression level when compared to non-transformed plants. Events B.3.1 and B.4.1, with similar increase in wood density and cell wall deposition, also showed a similar increase in walldof gene expression level related to control plants (6- and 7-fold increase, respectively) as shown in FIG. 13.

EXAMPLE 8

Growth Rate is Similar in Transformed and Non-Transformed Plants

Figure 14:
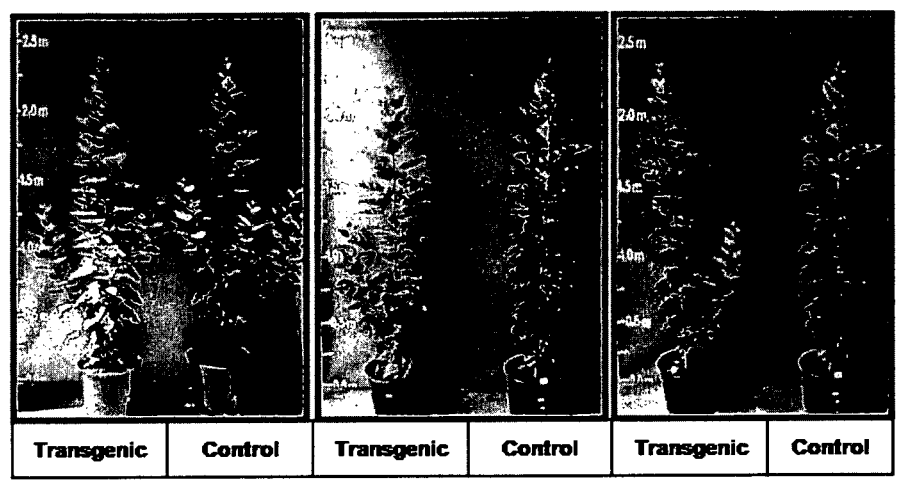
FIG. 14 shows plant phenotype comparisons between transgenic lines transformed with the plant expression plasmidial vector pALELLYX-DOF of the invention and control plants.

The allocation of carbon to increase the wall deposition and wood density did not interfere with the plant growth and development as shown by the plant growth rate (FIG. 14). The transformed plants grew with the same efficiency as the control plants after 2 months in the greenhouse.

EXAMPLE 9

Overexpression of Walldof Increases Cellulose Content

To analyze whether walldof overexpression modifies wood composition, greenhouse-grown plant stem material was ground with a Wiley mill to pass through a 40-60 mesh screen and then soxhlet extracted with acetone for 5 h. The extractive-free material was used for all further analyses. Lignin content was determined with a modified Klason, where extracted ground stem tissue (0.3 g) was treated with 3 ml of 72% $H_2SO_4$ according to Coleman et al., *Plant Biotechnol. J.*, 4:87-101 (2006). The dry crucibles were weighed to determine Klason (acid-insoluble lignin) lignin gravimetrically. The filtrate was also analysed for acid-soluble lignin by absorbance at 205 nm. Carbohydrate concentrations in the hydrolysate were determined by using high-performance liquid chromatography (HPLC) (DX-500; Dionex) equipped with an ion exchange PA1 (Dionex) column, a pulsed amperometric detector with a gold electrode, and a Spectra AS 3500 autoinjector (Spectra-Physics). Each experiment was run in duplicate. The determination of the S/G ratio of each extractive-free sample was obtained by nitrobenzene oxidation. Methods in Lignin Chemistry, eds. Lin and Vance, Springer Verlag, Berlin, 1992. See Table 2.

WALLDOF overexpressing plants presented up to 12% increased cellulose, and a general reduction in hemicellulose carbohydrates. As shown in Table 1, the reduction in hemicellulose content was accounted mainly by a decrease in mannose (as low as 42% of wild-type content in event A.4.2) and arabinose (as low as 72% of wild-type content in event A.4.2).

TABLE 1

Carbohydrate composition (% of dry wood weight) of stem wood in control and transgenic poplar.

| Lines | Glucose | Xylose | Mannose | Galactose | Arabinose | Rhamnose |
|---|---|---|---|---|---|---|
| Wild-type | 38.07 (0.17) | 18.27 (0.17) | 1.12 (0.08) | 0.80 (0.00) | 0.35 (0.02) | 0.46 (0.03) |

TABLE 1-continued

Carbohydrate composition (% of dry wood weight) of stem wood in control and transgenic poplar.

| Lines | Glucose | Xylose | Mannose | Galactose | Arabinose | Rhamnose |
|---|---|---|---|---|---|---|
| A.4.2 | 42.45 | 16.95 | 0.48 | 0.68 | 0.25 | 0.37 |
|  | (0.30) | (0.25) | (0.12) | (0.02) | (0.01) | (0.01) |
| B.3.1 | 42.10 | 17.35 | 0.54 | 0.75 | 0.26 | 0.41 |
|  | (0.20) | (0.05) | (0.06) | (0.01) | (0.01) | (0.01) |
| B.4.1 | 42.55 | 17.90 | 0.68 | 0.75 | 0.33 | 0.44 |
|  | (0.55) | (0.00) | (0.02) | (0.01) | (0.02) | (0.01) |
| A.1.10 | 39.10 | 18.40 | 1.21 | 0.85 | 0.37 | 0.48 |
|  | (0.30) | (0.20) | (0.09) | (0.00) | (0.02) | (0.01) |

Mean values and standard errors (in parentheses) are reported for duplicate analyses of n independent lines.
Wild-type, n = 3;
Transgenic lines, n = 2.
Carbohydrates data were analyzed by ANOVA. Values that are significantly different from wild-type are indicated in bold (Tukey test; $P < 0.05$).

TABLE 2

Lignin content and composition of stem wood in control and transgenic poplar.

| | Lignin (% dry wood weight) | | | Lignin monomers | | |
|---|---|---|---|---|---|---|
| | Acid | Acid | Total | (µmol/g Klason lignin) | | |
| Lines | insoluble | soluble | Lignin | Syringyl | Guaiacyl | S:G |
| Wild-type | 18.17 | 3.87 | 22.04 | 1,203.51 | 528.53 | 2.29 |
|  | (0.33) | (0.32) | (0.65) | (69.09) | (43.30) |  |
| A.4.2 | 19.02 | 2.57 | 21.59 | 858.39 | 599.21 | 1.43 |
|  | (0.36) | (0.15) | (0.22) | (37.19) | (8.27) |  |
| B.3.1 | 18.94 | 2.94 | 21.88 | 976.96 | 593.38 | 1.65 |
|  | (0.36) | (0.06) | (0.30) | (61.95) | (32.27) |  |
| B.4.1 | 17.98 | 3.22 | 21.20 | 929.96 | 512.67 | 1.81 |
|  | (0.06) | (0.26) | (0.32) | (79.13) | (15.52) |  |
| A.1.10 | 18.50 | 4.13 | 22.63 | 1,143.84 | 513.72 | 2.23 |
|  | (0.52) | (0.30) | (0.22) | (28.64) | (33.33) |  |

Mean values and standard errors (in parentheses) are reported for duplicate analyses of n independent lines.
Wild-type, n = 3;
Transgenic lines, n = 2.
Data was analyzed by ANOVA. Values that are significantly different from wild-type are indicated in bold (Tukey test; $P < 0.05$).

EXAMPLE 10

Walldof Affects Expression of Genes Involved in Nitrogen and Carbohydrate Metabolism To identify candidate target genes directly or indirectly controlled by the walldof transcription factor, microarray analyses were performed to compare overexpressing walldof line A.4.2 and wild-type plants.

Stems of three biological replicates of wild-type and three biological replicates of transgenic line A.4.2 were harvested, and immediately frozen in liquid nitrogen, and kept at −80° C. for RNA extraction. For RNA isolation, the stems were debarked, and the developing xylem was scraped off with a razor blade. Xylem was ground to a fine powder under liquid nitrogen, and total RNA was extracted from each sample using the procedure described by Chang et al., *Plant Mol. Biol. Rep.* 11:4 (1993). RNA quality was determined using an Agilent 2100 bioanalyzer. For each sample, 10 µg of total RNA was reverse transcribed, labeled, and hybridized to the Poplar Genome Array according to the manufacturer's protocols (Affymetrix). The Poplar Genome Array includes 61,251 probe sets representing more than 56,055 transcripts (Affymetrix).

GeneChip data analysis was performed using the BioConductor suite in R using the Affy package described by Gautier et al., *Bioinformatics* 20:307-315 (2004). The background correction, normalization, and expression value summarization was performed using Robust Multichip Average analysis. Present call probe sets was assigned by Affy Mas5calls function. Any gene with absent or marginal signal in all of the samples were removed from the analysis. Comparisons between transgenic plants and wild-type were performed using the Limma package. Smith, *Stat. Appl. Genet. Mol. Biol.*, 3:3 (2004). Differentially expressed genes were identified using the false discovery rate corrected t test. Benjamini and Hochberg, *J. R. Stat. Soc. Ser. B* 57:289-300 (1995). The corrected P value threshold was set to 0.05.

Xylem transcriptome analyses of walldof events using Affymetrix Genechip Poplar Genome Array identified 825 genes that are differentially expressed, including a set of genes involved with nitrogen and carbohydrate metabolism, cell wall synthesis and modification and phenylpropanoid metabolism.

Within nitrogen metabolism, the microarray data confirmed the down-regulated expression level of glutamate dehydrogenase genes GDH1 and GDH2. Furthermore, transcript levels of GS2, a chloroplast glutamine synthetase isoform, are elevated in the walldof overexpressing poplars. Since the ammonium liberated by the PAL reaction is reassimilated by glutamine synthetase, this increase is expected in the transformants.

In addition, the transcript levels of four genes encoding enzymes involved in the starch degradation (i.e., an alpha-amylase-like gene [AMY3], two alpha-glucan phosphorylase genes and an alpha-glucan dikinase [SEX1]) were elevated in the walldof-overexpressed line, whereas that of ADP-glucose pyrophosphorase large subunits [AGP2 and AGP3], were reduced. These data pointed to an increased breakdown of starch. We have analyzed total starch in transgenic plants (Table 3) and we have observed a decrease up to 32% in starch content in transgenic plants.

Related to cell wall organization, the transcript levels of nine putative arabinogalactan proteins (AGP) were altered. Seven were down-regulated and two were elevated.

The transcript levels of four genes whose expression levels are typically elevated during lignin formation were increased in the walldof-overexpressed line: four genes encoding laccases. Overall, the transcriptome analysis revealed differences in the metabolism of cell wall constituents (lignin, carbohydrates, and proteins) and of nitrogen and carbon metabolism.

TABLE 3

Starch content of stem wood in control and transgenic poplar.

| Lines | Total Starch (%) |
|---|---|
| A.4.2 | 5.02 |
| B.4.2 | 5.70 |
| Wild-type | 6.66 |

What is claimed is:

1. A method for increasing at least one of cell wall deposition and cellulose content, comprising:
effecting overexpression of a walldof DNA sequence in a transgenic plant transformed with a construct comprised of a walldof DNA sequence, and operably linked thereto, a promoter that is active in plant cells;
wherein said walldof DNA sequence is selected from the group consisting of SEQ ID NO:1 and sequences encoding a transcription factor having at least 90% sequence identity with SEQ ID NO:2, wherein said transcription factor increases cell wall deposition and/or increases cellulose content in a plant cell.

2. A method according to claim 1, wherein said transgenic plant is the product of a process comprising:
(a) providing regenerable plant material that is transformed with a construct comprised of the walldof DNA sequence and, operably linked thereto, a promoter that is active in plant cells; and then
(b) subjecting said material or plants regenerated from said material to a selection for which at least one selection criterion is increased cell wall deposition or increased cellulose content, relative to a non-transformed state.

3. A method according to claim 2, wherein said promoter is a xylem-preferred promoter.

4. A method according to claim 2, wherein said promoter is a constitutive promoter.

5. A method according to claim 1, wherein said walldof sequence encodes the amino acid sequence set out in SEQ ID NO: 2.

6. A method according to claim 5, wherein said walldof sequence is the sequence set out in SEQ ID NO: 1.

7. A construct comprised of:
a walldof DNA sequence selected from the group consisting of SEQ ID NO:1 and sequences encoding a transcription factor having at least 90% sequence identity with SEQ ID NO:2, wherein said transcription factor increases cell wall deposition and/or increases cellulose content;
and, operably linked thereto, a heterologous promoter that is active in plant cells.

8. A transgenic plant cell comprising the construct of claim 7.

9. A transgenic plant comprising the construct of claim 7, wherein said plant expresses said walldof DNA sequence, such that said plant is characterized by increased biomass density, relative to a non-transformed state.

10. A method for increasing cellulose content, comprising:
effecting overexpression of a walldof DNA sequence in a transgenic plant transformed with a construct comprised of a walldof DNA sequence selected from the group consisting of SEQ ID NO:1 and sequences encoding a transcription factor having at least 90% sequence identity with SEQ ID NO:2, wherein said transcription factor increases cellulose content in a plant cell.

11. A processed plant product comprising a detectable amount of the construct of claim 7.

12. The processed plant product of claim 11, wherein said product comprises a feed, a meal, a flour, and extract, a pulp, or a homogenate wherein said feed, meal, flour, extract, pulp, or homogenate is obtained from at least one plant part.

13. The processed plant product of claim 12, wherein said plant part is a stem, a leaf, a root, a flower, cambium, wood, a tuber, or a seed.

\* \* \* \* \*